US008143030B2

(12) United States Patent
Maxham et al.

(10) Patent No.: US 8,143,030 B2
(45) Date of Patent: Mar. 27, 2012

(54) INTERMITTENT DETECTION DURING ANALYTICAL REACTIONS

(75) Inventors: Kenneth Mark Maxham, Redwood City, CA (US); Jon Sorenson, Alameda, CA (US); John Eid, San Francisco, CA (US); Patrick Marks, San Francisco, CA (US); Kevin Travers, Santa Clara, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 270 days.

(21) Appl. No.: 12/413,226

(22) Filed: Mar. 27, 2009

(65) Prior Publication Data

US 2010/0075309 A1 Mar. 25, 2010

Related U.S. Application Data

(60) Provisional application No. 61/139,402, filed on Dec. 19, 2008, provisional application No. 61/099,696, filed on Sep. 24, 2008.

(51) Int. Cl.
*C12P 19/34* (2006.01)
*C12Q 1/68* (2006.01)

(52) U.S. Cl. ........................................ 435/91.2; 435/6.1

(58) Field of Classification Search ................. 435/91.2, 435/6.1
See application file for complete search history.

(56) References Cited

U.S. PATENT DOCUMENTS

| | | | |
|---|---|---|---|
| 5,001,050 A | 3/1991 | Blanco et al. |
| 5,198,543 A | 3/1993 | Blanco et al. |
| 5,350,686 A | 9/1994 | Jhingah |
| 5,470,724 A | 11/1995 | Ahem |
| 5,547,839 A | 8/1996 | Dower |
| 5,576,204 A | 11/1996 | Blanco et al. |
| 5,648,245 A | 7/1997 | Fire et al. |
| 5,674,683 A | 10/1997 | Kool |
| 5,674,716 A | 10/1997 | Tabor et al. |
| 5,714,320 A | 2/1998 | Kool |
| 5,854,033 A | 12/1998 | Lizardi |
| 6,210,891 B1 | 4/2001 | Nyren et al. |
| 6,210,896 B1 | 4/2001 | Chan |
| 6,255,083 B1 | 7/2001 | Williams |
| 6,261,808 B1 | 7/2001 | Auerbach |
| 6,369,038 B1 | 4/2002 | Blumenfeld et al. |
| 6,451,563 B1 | 9/2002 | Wittig et al. |
| 6,498,023 B1 | 12/2002 | Abarzua |
| 6,787,308 B2 | 9/2004 | Balasubramanian |
| 6,917,726 B2 | 7/2005 | Levene et al. |
| 7,013,054 B2 | 3/2006 | Levene et al. |
| 7,033,764 B2 | 4/2006 | Korlach et al. |
| 7,045,362 B2 | 5/2006 | Hartwich et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,170,050 B2 | 1/2007 | Korlach et al. |
| 7,181,122 B1 | 2/2007 | Levene et al. |
| 7,229,799 B2 | 6/2007 | Williams et al. |
| 7,282,337 B1 | 10/2007 | Harris et al. |
| 7,292,742 B2 | 11/2007 | Levene et al. |
| 7,361,466 B2 | 4/2008 | Korlach et al. |
| 7,368,265 B2 | 5/2008 | Brenner et al. |
| 7,416,844 B2 | 8/2008 | Korlach et al. |
| 7,476,503 B2 | 1/2009 | Turner et al. |
| 7,485,424 B2 | 2/2009 | Korlach et al. |
| 7,601,495 B2 | 10/2009 | Chen et al. |
| 7,601,499 B2 | 10/2009 | Berka et al. |
| 7,700,287 B2 | 4/2010 | Chen et al. |
| 7,754,429 B2 | 7/2010 | Rigatti et al. |
| 7,767,400 B2 | 8/2010 | Harris et al. |
| 2001/0030290 A1 | 10/2001 | Stern |
| 2003/0044781 A1 | 3/2003 | Korlach et al. |
| 2003/0096253 A1 | 5/2003 | Nelson et al. |
| 2003/0143550 A1 | 7/2003 | Green et al. |
| 2003/0190647 A1 | 10/2003 | Odera |
| 2003/0207279 A1 | 11/2003 | Crothers et al. |
| 2003/0213771 A1 | 11/2003 | Ohshita et al. |
| 2003/0215862 A1 | 11/2003 | Parce et al. |
| 2004/0048300 A1 | 3/2004 | Sood et al. |
| 2004/0152119 A1 | 8/2004 | Sood et al. |
| 2004/0203008 A1 | 10/2004 | Uemori et al. |
| 2004/0224319 A1 | 11/2004 | Sood et al. |
| 2004/0259082 A1 | 12/2004 | Williams |
| 2005/0176035 A1 | 8/2005 | Crothers |

(Continued)

FOREIGN PATENT DOCUMENTS

EP    1225234 B1    11/2007

(Continued)

OTHER PUBLICATIONS

Koonin et al. "Computer-assisted dissection of rolling circle DNA replication" Biosystems (1993) 30(1-3):241-268.

(Continued)

*Primary Examiner* — Gary Benzion
*Assistant Examiner* — Cynthia Wilder
(74) *Attorney, Agent, or Firm* — Deana A. Arnold

(57) ABSTRACT

Methods, devices, and systems for performing intermittent detection during analytical reactions are provided. Such methods facilitate collection of reaction data from disparate reaction times. Further, such methods are useful for reducing photo-induced damage of one or more reactants in an illuminated analytical reaction at a given reaction time. In preferred embodiments, the reaction mixture is subjected to at least one illuminated and non-illuminated period and allowed to proceed such that the time in which the reaction mixture is illuminated is less than a photo-induced damage threshold period.

19 Claims, 11 Drawing Sheets

U.S. PATENT DOCUMENTS

| | | | |
|---|---|---|---|
| 2006/0061754 A1 | 3/2006 | Turner et al. | |
| 2006/0292611 A1 | 12/2006 | Berka et al. | |
| 2007/0062934 A1 | 3/2007 | King | |
| 2007/0161017 A1 | 7/2007 | Eid et al. | |
| 2007/0178482 A1 | 8/2007 | Lezhava et al. | |
| 2007/0269825 A1 | 11/2007 | Wang et al. | |
| 2008/0009007 A1* | 1/2008 | Lyle et al. | 435/6 |
| 2008/0026393 A1 | 1/2008 | Mindrinos et al. | |
| 2008/0176241 A1* | 7/2008 | Eid et al. | 435/6 |
| 2008/0233575 A1 | 9/2008 | Harris et al. | |
| 2009/0087850 A1* | 4/2009 | Eid et al. | 435/6 |
| 2009/0088327 A1* | 4/2009 | Rigatti et al. | 506/4 |
| 2009/0197257 A1 | 8/2009 | Harris | |
| 2009/0269771 A1 | 10/2009 | Schroeder | |
| 2009/0305248 A1 | 12/2009 | Lander et al. | |

FOREIGN PATENT DOCUMENTS

| | | |
|---|---|---|
| EP | 1907573 B1 | 1/2010 |
| WO | WO91/06678 | 5/1991 |
| WO | 9416090 A1 | 7/1994 |
| WO | WO96/27025 | 9/1996 |
| WO | WO9905315 | 2/1999 |
| WO | 2007003017 A1 | 1/2007 |
| WO | 2007010263 A2 | 1/2007 |
| WO | 2007070572 | 6/2007 |
| WO | 2008058282 | 5/2008 |
| WO | 2009124255 A2 | 10/2009 |

OTHER PUBLICATIONS

Kuhn et al., "Rolling-circle ampificaition under topological constraints" Nucl Acids Res (2002) 30(2):574-580.

Matray, T.J. et al. "A specific partner for abasic damage in DNA" Nature (1999) 399:704-708.

Novick "Contrasting lifestyles of rolling-circle phages and plasmids" Trends Biochem Sci (1998) 23(11):434-438.

Spinella et al., "Tandem arrayed ligation of expressed sequence tags (TALEST): a new method for generating global gene expression profiles" Nucl Acids Res (1999) 27(18):e22-e22.

Velculescu et al. "Serial analysis of gene expression" Science (1995) 270(5235): 484-487.

Hormozdiari, et al. "Combinatorial algorithms for structural variation detection in high-throughput sequenced genomes, " Genome Research (2009) 19:1270-1278.

Lee, et al., "A robust framework for detecting structural variations in a genome," Bioinformatics (2008) 24:i59-i67.

Margulies, et al., "Genome sequencing in microfabricated high-density picolitre reactors," Nature (2005), 437:376-382.

Pedler, "Occupation Times for Two State Markov Chains," Journ Appl Probability (1971), 8(2):381-90.

Svoboda, et al., "Fluctuation analysis of motor protein movement and single enzyme kinetics," PNAS (1994), 91:11782-86.

International Search Report and Written Opinion dated Apr. 29, 2010 for related case PCT/US2009/005169.

International Search Report and Written Opinion dated Oct. 27, 2009 for related case PCT/US2009/001930.

International Preliminary Report on Patentability dated Oct. 7, 2010 for related case PCT/US2009/001930.

International Search Report and Written Opinion dated Nov. 17, 2009 for related case PCT/US2009/001926.

Metzker, M.I., "Emerging Technologies in DNA Sequencing," Genome Research (2005) 15:1767-1776.

A. Bashir, et al., "Evaluation of Paired-End Sequencing Strategies for Detection of Genome Rearrangements in Cancer", PLoS Computational Biology, Apr. 2008, vol. 4, Issue 4, pp. 1-14.

John Eid, et al., "Real-Time DNA Sequencing from Single Polymerase Molecules", Science 323, 133 (2009).

Timothy D. Harris, et al., "Single-Molecule DNA Sequencing of a Viral Genome", Science 320, 106 (2008).

Hong, Y. S., Hogan, J. R., et al., Mol Genet Genomics, (2003) 268: pp. 720-728.

Jan O. Korbel, et al., "Paired-End Mapping Reveals Extensive Structural Variation in the Human Genome", Science vol. 318, Oct. 19, 2007, pp. 420-426.

M. J. Levene, et al., "Zero-Mode Waveguides for Single-Molecule Analysis at High Concentrations", Science, vol. 299, Jan. 31, 2003, pp. 682-686.

Myers, Gene, "Whole-Genome DNA Sequencing", May-Jun. 1999, IEEE, pp. 33-43.

Jeffrey Reifenberger, et al., (2009) Advances in Genome Biology and Technology (AGBT) abstract; Feb. 4-7, 2009.

Jeffrey Reifenberger, et al., (2009) Biophysical Society $53^{rd}$ Annual Meeting abstract; Feb. 28, 2009.

Michael Smith, et al., "Genomic Sequence Sampling: a strategy for high resolution sequence-based physical mapping of complex genomes", Nature Genetics, vol. 7, May 1994, pp. 40-47.

Technology Spotlight: Illumina Sequencing Technology, current of Oct. 8, 2008, pp. 1-4.

Stanislav Volik, et al., End-Sequence Profiling: Sequence-based analysis of aberrant genomes, PNAS, Jun. 2003, vol. 100, No. 13, pp. 7696-7701.

Thomas Keane and Zemin Ning, "Assessing Assemblability of Reads from New Sequencing Platforms", Wellcome Trust Poster. p. 1.

Graham Wiley, et al., "Methods for Generating Shotgun and Mixed Shotgun/Paired-End Libraries for the 454 DNA Sequence", Current Protocols in Human Genetics, 2009, pp. 1-21. Chapter 18: Unit 18.1.

International Preliminary Report on Patentability dated Apr. 7, 2011 for related case PCT/US2009/005169.

International Search Report and Written Opinion dated Nov. 3, 2009 for related case PCT/US2009/001927.

International Preliminary Report on Patentability dated Apr. 7, 2011 for related case PCT/US2009/001927.

* cited by examiner

A.

B.

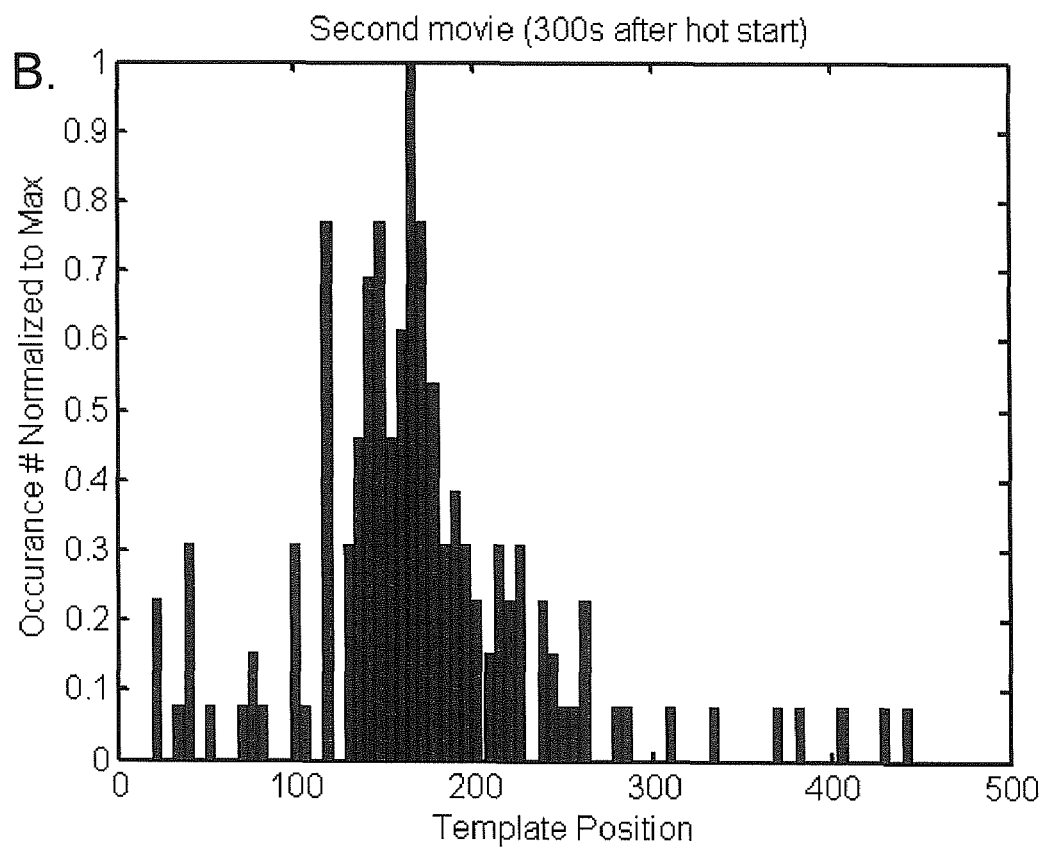
Figure 8, cont.

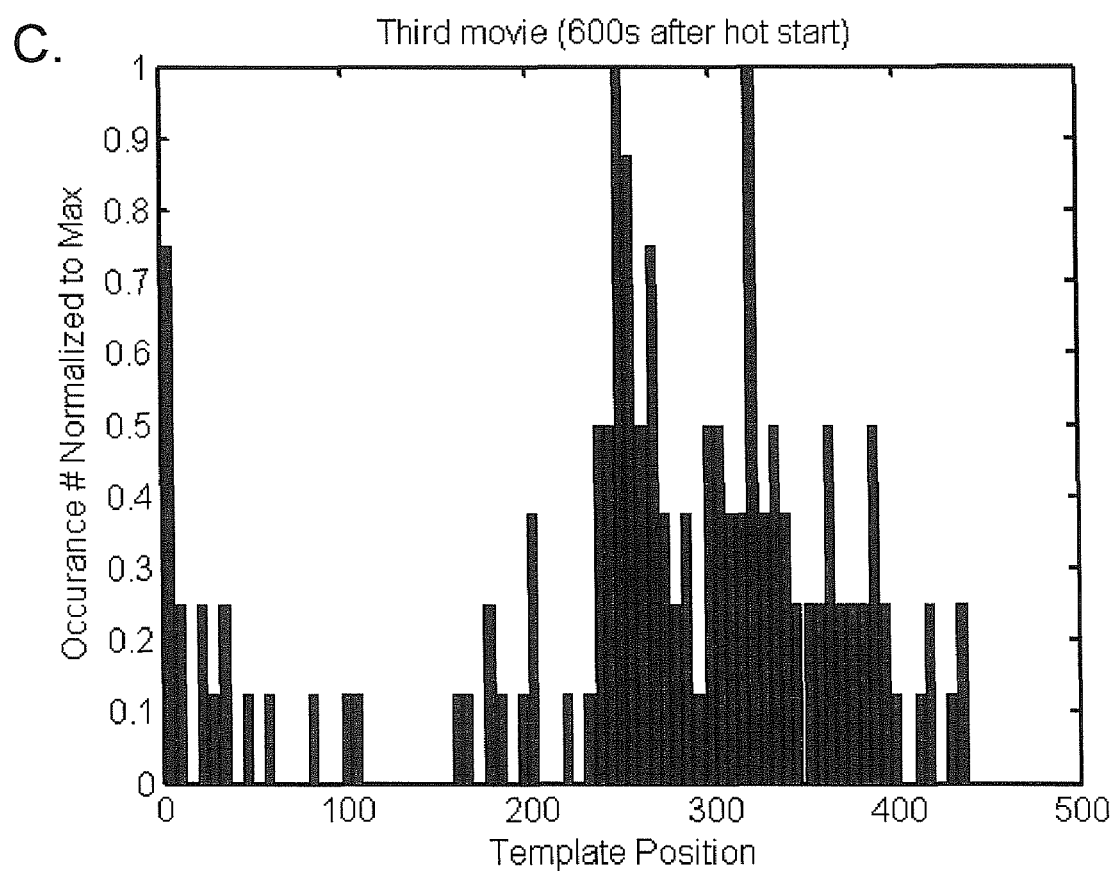
Figure 8, cont.

INTERMITTENT DETECTION DURING ANALYTICAL REACTIONS

CROSS-REFERENCE TO RELATED APPLICATIONS

This application claims the benefit of U.S. Provisional Application No. 61/099,696, filed Sep. 24, 2008, and U.S. Provisional Application No. 61/139,402, filed Dec. 19, 2008, the full disclosures of which are incorporated herein by reference in their entireties for all purposes.

This application is also related to U.S. Provisional Application No. 61/072,160, filed Mar. 28, 2008, U.S. patent application Ser. No. 12/383,855, filed Mar. 27, 2009 and U.S. patent application Ser. No. 12/413,258, filed Mar. 27, 2009, all of which are incorporated herein by reference in their entireties for all purposes.

STATEMENT REGARDING FEDERALLY SPONSORED RESEARCH

Not Applicable.

BACKGROUND OF THE INVENTION

The use of optically detectable labeling groups, and particularly those groups having high quantum yields, e.g., fluorescent or chemiluminescent groups, is ubiquitous throughout the fields of analytical chemistry, biochemistry, and biology. In particular, by providing a highly visible signal associated with a given reaction, one can better monitor that reaction as well as any potential effectors of that reaction. Such analyses are the basic tools of life science research in genomics, diagnostics, pharmaceutical research, and related fields.

Such analyses have generally been performed under conditions where the amounts of reactants are present far in excess of what is required for the reaction in question. The result of this excess is to provide ample detectability, as well as to compensate for any damage caused by the detection system and allow for signal detection with minimal impact on the reactants. For example, analyses based on fluorescent labeling groups generally require the use of an excitation radiation source directed at the reaction mixture to excite the fluorescent labeling group, which is then separately detectable. However, one drawback to the use of optically detectable labeling groups is that prolonged exposure of chemical and biochemical reactants to such light sources, alone, or when in the presence of other components, e.g., the fluorescent groups, can damage such reactants. The traditional solution to this drawback is to have the reactants present so far in excess that the number of undamaged reactant molecules far outnumbers the damaged reactant molecules, thus minimizing or negating the effects of the photo-induced damage.

A variety of analytical techniques currently being explored deviate from the traditional techniques. In particular, many reactions are based on increasingly smaller amounts of reagents, e.g., in microfluidic or nanofluidic reaction vessels or channels, or in "single molecule" analyses. Such low reactant volumes are increasingly important in many high throughput applications, such as microarrays. The use of smaller reactant volumes offers challenges to the use of optical detection systems. When smaller reactant volumes are used, damage to reactants, such as from exposure to light sources for fluorescent detection, can become problematic and have a dramatic impact on the operation of a given analysis. In other cases, other reaction conditions may impact the processivity, rate, fidelity, or duration of the reaction, including salt or buffer conditions, pH, temperature, or even inunobilization of reaction components within observable reaction regions. In many cases, the effects of these different reaction or environmental conditions can degrade the performance of the system over time. This can be particularly detrimental, for example, in real-time analysis of reactions that include fluorescent reagents that can expose multiple different reactions components to optical energy. In addition, smaller reactant volumes can lead to limitations in the amount of signal generated upon application of optical energy.

Further, in the case of sequencing-by-synthesis applications, an additional challenge has been to develop ways to effectively sequence noncontiguous portions of a template nucleic acid on a single molecule. This challenge is exacerbated in template nucleic acids that contain highly repetitive sequence and/or are hundreds or thousands of nucleotides in length, such as certain genomic DNA fragments. The difficulty generating such noncontiguous reads from a single template has hampered efforts to construct consensus sequences for long templates, for example, in genome sequencing projects.

As such, methods and systems that result in enhanced reaction performance, such as an increase in processivity, rate, fidelity, or duration of a reaction of interest, would provide useful improvements to the methods and compositions currently available. For example, methods, devices, and systems that increase reaction performance by, e.g., mitigating to some extent photo-induced damage in a reaction of interest and/or increasing various other performance metrics for the reaction would be particularly useful.

BRIEF SUMMARY OF THE INVENTION

In a general sense, the methods provided herein implement intermittent detection of analytical reactions as a means to collect reliable data from times during the reaction that are less or not able to be analyzed if detection is constant throughout the reaction. In particular, certain detection methods can cause damage to reaction components, and such intermittent detection allows the damage to be avoided or at least delayed, thereby facilitating detection of the reaction at later stages. For example, if a detection method causes a reduction in processivity of a polymerase enzyme, then intermittent detection would allow data collection at noncontiguous regions of a template nucleic acid that extend farther from the initial binding site of the polymerase on the template than would be achievable under constant detection. Further, some detection methods have limits on how much data or for how long a time data may be generated in a single reaction, and intermittent detection of such a reaction can allow this data to be collected from various stages of a reaction, thereby increasing the flexibility of the investigator to spread out the data collection over multiple stages of a reaction. In certain aspects, the present invention is particularly suitable to characterization of analytical reactions in real time, that is, during the course of the reaction. In certain aspects, the present invention is particularly suitable to characterization of single molecules or molecular complexes monitored in analytical reactions, for example, single enzymes, nucleotides, polynucleotides, and complexes thereof.

In certain aspects, the present invention is directed to methods, devices, and systems for obtaining sequence data from discontiguous portions of single nucleic acid templates. The methods generally comprise providing a monitorable sequencing reaction comprising a polymerase, template, and primer sequence, as well as the various types of nucleotides or nucleotide analogs that are to be incorporated by the polymerase enzyme in the template-directed primer extension reaction. Typically, at least one or more or all of the nucleotides or nucleotide analogs are embodied with a detectable property that permits their identification upon or following incorporation. In the context of the present invention, the sequence data for a first portion of a template nucleic acid is acquired during a first stage of the reaction under a first set of reaction conditions that includes at least one reaction condition that results in degraded performance of the reaction, but that may contribute to the detectability of the nucleotides being incorporated. During a second stage of the reaction, the degradative influence is eliminated or reduced, which may result in an inability or a reduced ability to obtain sequence data from a second portion of the template nucleic acid, but where the second portion of the template nucleic acid is contiguous with the first portion. Subsequently, the reaction condition resulting in degraded performance is reinstated and sequence data is obtained for a third portion of the template nucleic acid during a third stage of the reaction, but where the third portion of the sequence is not contiguous with the first portion of the sequence, but is contiguous with the second portion. The elimination or reduction of the degradative influence during the second stage of the reaction may be accomplished by changing or shortening one or more reaction conditions underlying degradative reaction performance, e.g., by changing one or more reaction conditions (e.g., temperature, pH, exposure to radiation, physical manipulation, etc.), and in particular may involve altering a reaction condition related to detection of one or more aspects or products of the reaction. However, in preferred embodiments, nucleotides or nucleotide analogs having the detectable property are present in the reaction mixture during all stages of the reaction, including stages in which the degradative influence is eliminated or reduced; as such, the reaction condition changed in stage two of such an embodiment would not comprise removal or dilution of such detectable nucleotides or nucleotide analogs.

In certain aspects, the present invention is generally directed to methods, devices, and systems for enhancing the performance of illuminated reactions. The term "illuminated reactions" as used herein refers to reactions which are exposed to an optical energy source. In certain preferred embodiments, illuminated reactions comprise one or more fluorescent or fluorogenic reactants. Typically, such illumination is provided in order to observe the generation and/or consumption of reactants or products that possess a particular optical characteristic indicative of their presence, such as a shift in the absorbance spectrum and/or emission spectrum of the reaction mixture or its components. In some aspects, enhancing the performance of an illuminated reaction means increasing the processivity, rate, fidelity, and/or duration of the reaction. For example, enhancing the performance of an illuminated reaction can involve reducing or limiting the effects of photo-induced damage during the reaction. The term "photo-induced damage" refers generally to any direct or indirect impact of illumination on one or more reagents in a reaction resulting in a negative impact upon that reaction.

In certain aspects, methods of the invention useful for characterizing an analytical reaction comprise preparing a reaction mixture and initiating the analytical reaction therein, subjecting the reaction mixture to at least one detection period and at least one non-detection period during the course of the analytical reaction, collecting data during both the detection period(s) and the non-detection period(s), and combining the collected data to characterize the analytical reaction. In certain embodiments, the analytical reaction comprises an enzyme that exhibits an improvement in performance as compared to its performance in the analytical reaction under constant illumination, and such improvement may be related to various aspects of enzyme activity, e.g., processivity, fidelity, rate, duration of the analytical reaction, and the like. In certain embodiments, stop or pause points are used to control the activity of the enzyme, and such stop or pause points may comprise elements such as large photolabile groups, strand-binding moieties, non-native bases, and others well known in the art. In certain preferred embodiments, the one or more detection periods are illuminated periods and the one or more non-detection periods are non-illuminated periods. In certain preferred embodiments, a plurality of analytical reactions disposed on a solid support are characterized, preferably in a coordinated fashion as described elsewhere herein.

In certain preferred embodiments, the analytical reaction is a sequencing reaction that generates sequence reads from a single nucleic acid template during the detection period(s) but not during the non-detection period(s). For example, the analytical reaction can comprise at least two or more detection periods and can generate a plurality of noncontiguous reads from the single nucleic acid template. In some embodiments, the single nucleic acid template is at least 100 bases in length and/or comprises multiple repeat sequences. In certain embodiments, the sequencing reaction comprises passage of the single nucleic acid template through a nanopore, and in other embodiments the sequencing reaction comprises primer extension by a polymerase enzyme.

The analytical reaction may optionally be a processive reaction monitored in real time, i.e., during the course of the processive reaction. In preferred embodiments, such a processive reaction is carried out by a processive enzyme that can repetitively execute its catalytic function, thereby completing multiple sequential steps of the reaction. For example, a processive polymerization reaction can comprise a polymerase enzyme repetitively incorporating multiple nucleotides or nucleotide analogs, as long as such are available to the polymerase within the reaction mixture, e.g., without stalling on the template nucleic acid. Such a processive polymerization reaction can be prevented by incorporation of nucleotides or nucleotide analogs that contain groups that block additional incorporation events, e.g., certain labeling groups or other chemical modifications.

In certain preferred embodiments, the analytical reaction comprises at least one component comprising a detectable label, e.g., a fluorescently labeled nucleotide. In certain embodiments, the labeled component is present throughout the course of the analytical reaction, i.e., during both the detection and the non-detection periods. The method may further comprise an optical system to collect the data during the detection period, but optionally not to collect the data during the non-detection period.

In certain aspects, methods of the invention comprise providing a substrate having a reaction mixture disposed thereon and illuminating the reaction mixture on the substrate with an excitation illumination for multiple, noncontiguous periods during the course of the reaction, thereby subjecting the reaction mixture to intermittent excitation illumination. In some embodiments, the reaction mixture comprises first reactant and a second reactant, wherein an amount of photo-induced damage to the first reactant occurs as a result of interaction between the first reactant and the second reactant under excitation illumination. In certain embodiments, the method further comprises monitoring a reaction between the first and second reactants during illumination and collecting the data generated therefrom. In some embodiments, the reaction is a base extension reaction and/or the first reactant is a polymerase enzyme. In certain embodiments, the second reactant is a fluorogenic or fluorescent molecule.

In yet another aspect, the methods are useful for mitigating photo-induced damage in an illuminated reaction by subjecting the illuminated reaction to intermittent illumination rather than constant illumination. For example, certain methods of the invention monitor a reaction mixture comprising at least one enzyme and a fluorescent or fluorogenic substrate for the enzyme, wherein interaction of the enzyme and the substrate under excitation illumination can result in altered activity of the enzyme, e.g if such excitation illumination is present over an extended period of time. Such methods can comprise directing intermittent excitation illumination at a first observation region for a first period that is less than a photo-induced damage threshold period under the intermittent illumination conditions, but that is greater than a photo-induced damage threshold period under constant illumination conditions. As such, certain aspects of the invention lengthen a photo-induced damage threshold period for an analytical reaction through intermittent inactivation of the excitation illumination source since the photo-induced damage threshold period under intermittent illumination is longer than the photo-induced damage threshold period under constant illumination.

In a related aspect, the invention also provides methods of performing an enzyme reaction, comprising providing an enzyme within a first observation region, contacting the enzyme with a fluorescent or fluorogenic substrate for the enzyme, and directing an excitation radiation at and detecting signals from the first observation region for a period that is less than a photo-induced damage threshold period under intermittent illumination conditions, but that is greater than a photo-induced damage threshold period under constant illumination conditions.

In further aspects, the invention provides methods of monitoring a base extension reaction, comprising providing a polymerase enzyme within a first observation region, contacting the polymerase with at least a first fluorescent or fluorogenic nucleotide analog, and monitoring a fluorescent signal emitted from the first observation region in response to illumination with excitation radiation for a period that is less than a photo-induced damage threshold period under intermittent illumination conditions, but that is greater than a photo-induced damage threshold period under constant illumination conditions.

In addition, the invention provides methods for generating a plurality of noncontiguous sequence reads from a single nucleic acid template molecule. Such methods generally comprise preparing a reaction mixture comprising the template molecule, a polymerase enzyme, and a set of differentially labeled nucleotides or nucleotide analogs, wherein the set comprises at least one type of nucleotide or nucleotide analog for each of the natural nucleobases (A, T, C, and G). The polymerization reaction is initiated, the polymerase begins processive incorporation of the labeled nucleotides or nucleotide analogs into a nascent nucleic acid strand, and during such incorporation the reaction is monitored by optical means to detect incorporation events, thereby generating a first sequence read. In a subsequent step, the labeled nucleotides or analogs are replaced with unlabeled nucleotides or nucleotide analogs and the polymerization is allowed to proceed without detecting incorporation events. Subsequently, the unlabeled nucleotides or analogs are replaced with labeled nucleotides or nucleotide analogs and the polymerization is allowed to proceed once again with real time detection of incorporation events, thereby generating a second sequence read that is noncontiguous to the first sequence read. The substitution of labeled for unlabeled, and unlabeled for labeled, nucleotides and nucleotide analogs can be repeated multiple times to generate a plurality of noncontiguous sequence reads, each of the plurality generated during a period when the labeled nucleotides or nucleotide analogs are being incorporated into the nascent strand and such incorporation is being detected in real time.

In certain aspects, devices of the invention can comprise a solid support (e.g., substrate) having an observation region, a first reactant immobilized within the observation region, and a second reactant disposed within the observation region, and a means for subjecting the observation region to at least one illuminated period and at least one non-illuminated period. In certain embodiments, interaction between the first and second reactants under excitation illumination causes photo-induced damage to the first reactant, and further wherein the photo-induced damage is reduced by subjecting the observation region to intermittent illumination. In some embodiments, the first reactant is an enzyme (e.g., a polymerase), the second reactant (e.g., a nucleotide) has a detectable label (e.g., fluorescent label), and/or the observation region is within a zero-mode waveguide. The means for subjecting the observation region to one or more an illuminated and non-illuminated periods may comprise, e.g., a laser, laser diode, light-emitting diode, ultra-violet lightbulb, white light source, a mask, a diffraction grating, an arrayed waveguide grating, an optic fiber, an optical switch, a mirror, a lens, a collimator, an optical attenuator, a filter, a prism, a planar waveguide, a wave-plate, a delay line, a movable support coupled with the substrate, and a movable illumination source, and the like. The device may further comprise a means for collecting the data during the illuminated period(s), such as an optical train, e.g., operably coupled to a machine comprising machine-readable medium onto which such data may be written and stored.

In further aspects, the invention provides systems for performing intermittent detection of an analytical reaction comprising reagents for the analytical reaction disposed on a solid support, a mounting stage configured to receive the solid support, an optical train positioned to be in optical communication with at least a portion of the solid support detect signals emanating therefrom, a means for subjecting the portion of the solid support to at least one detection period and at least one non-detection period, a translation system operably coupled to the mounting stage or the optical train for moving one of the optical train and the solid support relative to the other, and a data processing system operably coupled to the optical train. In certain preferred embodiments, the analytical reaction is a sequencing reaction and/or the solid support comprises at least one zero-mode waveguide.

In still other aspects, the invention provides systems for analyzing an illuminated reaction that is susceptible to photo-induced damage when illuminated for a period longer than an photo-induced damage threshold period, comprising a solid support having reagents for the reaction disposed thereon, a mounting stage supporting the solid support and configured to receive the solid support, an optical train positioned to be in optical communication with at least a portion of the solid support to illuminate the portion of the solid support and detect signals emanating therefrom, a means for subjecting the portion of the solid support to at least one detection period and at least one non-detection period, and a translation system operably coupled to the mounting stage or the optical train for moving one of the optical train and the solid support relative to the other. In some embodiments, the illuminated reaction is a sequencing reaction, e.g., a nucleotide sequencing-by-synthesis reaction. In certain embodiments, the solid support comprises at least one optical confinement, e.g., a zero-mode waveguide.

In still further aspects of the invention, machine-implemented methods for transforming nucleotide sequence read data into consensus sequence data, wherein the nucleotide sequence read data is generated by sequencing a target region of a template nucleic acid multiple times, and the consensus sequence data is representative of a most likely actual sequence of the template nucleic acid. Such machine-implemented methods can comprise various steps, such as a) mapping the nucleotide sequence data to a target sequence using a local alignment method that produces a set of local alignments comprising an optimal local alignment and sub-optimal local alignments, b) enumerating the set of local alignments, c) constructing a weighted directed graph wherein each local alignment in the set of local alignments is represented as a node, thereby generating a set of nodes in the weighted directed graph, d) drawing edges between pairs of nodes in the weighted directed graph if the pair represents a potential reconstruction of the template nucleic acid, e) assigning weights to the edges drawn in step d, wherein a given weight for a given edge represents the log-likelihood that a given pair of nodes connected by the given edge is truly a reconstruction of the template nucleic acid, f) finding the shortest path to each node in the weighted directed graph, thereby generating a set of shortest paths for the weighted directed graph, g) ranking the set of shortest paths to determine the best assignment, and h) storing the results of steps a-g on a machine-readable medium. In certain embodiments, the steps of the machine implemented methods are performed via a user interface implemented in a machine that comprises instructions stored in machine-readable medium and a processor that executes the instructions. Also provided are computer program products comprising a computer usable medium having computer readable program code embodied therein, said computer readable program code adapted to be executed to implement the machine-implemented methods of the invention, and machine-readable medium on which the results of the method steps are stored.

BRIEF DESCRIPTION OF THE DRAWINGS

FIG. 5A illustrates a solid support comprising four quadrants, each quadrant containing a different sample. FIG. 5B illustrates a mask design for selective illumination of the substrate. FIGS. 5C and 5D demonstrate various positions of the mask on the solid support.

FIG. 8A provides data from a two-minute interval beginning at initiation of the reactions, i.e., from 0-120 seconds. FIG. 8B provides data from a second two-minute interval from 300-420 seconds. FIG. 8C provides data from a third two-minute interval from 600-720 seconds.

DETAILED DESCRIPTION OF THE INVENTION

Figure 1:
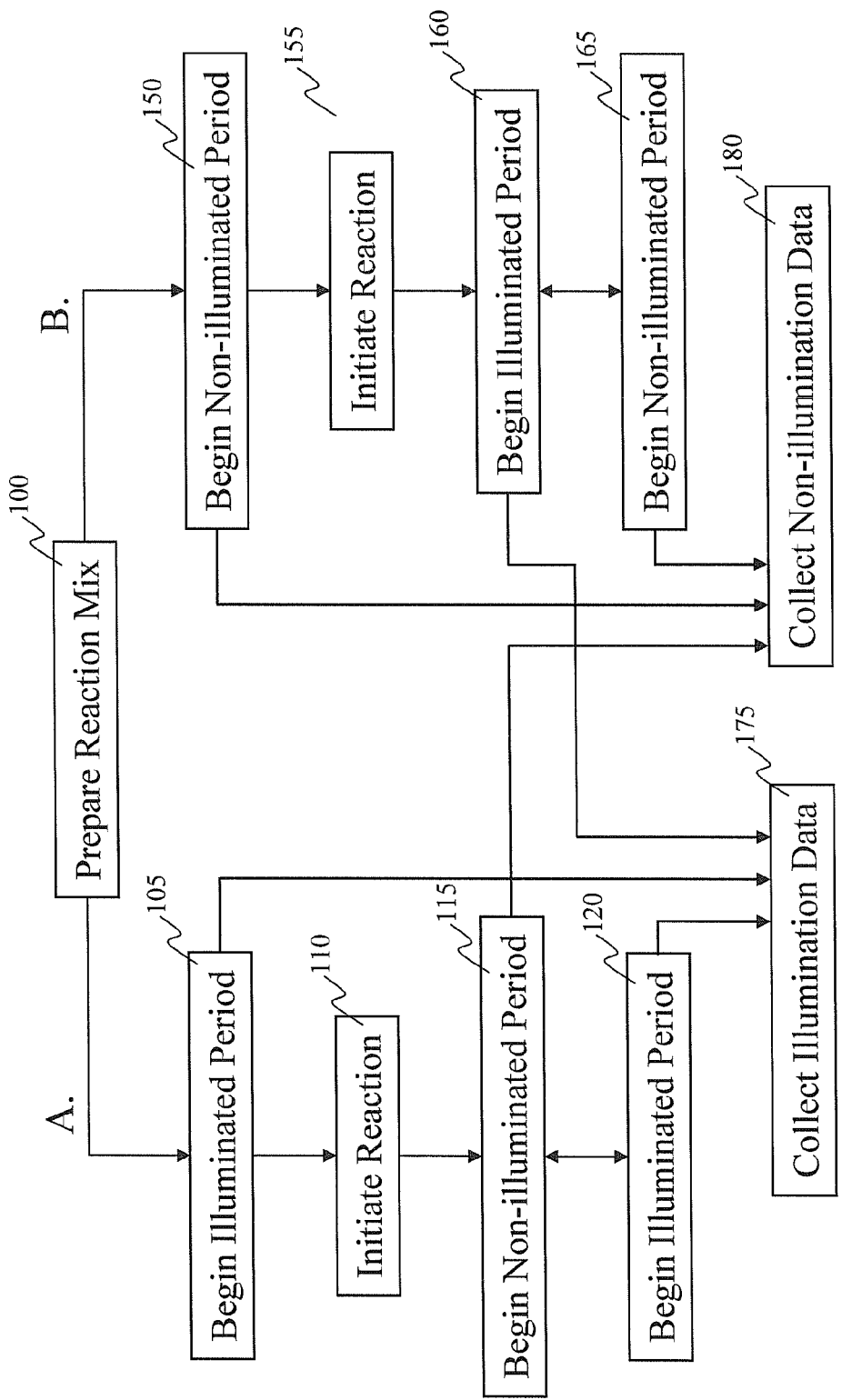
FIG. 1 provides exemplary embodiments of methods for intermittent illumination of analytical reactions, whether illumination is initiated before (A) or after (B) initiation of the reaction.

Unless defined otherwise, all technical and scientific terms used herein have the same meaning as commonly understood by one of ordinary skill in the art to which this invention pertains. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth. Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. Although a number of methods and materials similar or equivalent to those described herein can be used in the practice of the present invention, the preferred materials and methods are described herein.

I. GENERAL

In a general sense, the methods, devices, and systems provided herein implement intermittent detection of analytical reactions as a means to collect reliable data from times during the reaction that are less or not able to be analyzed if detection is constant throughout the reaction. In particular, certain detection methods can cause damage to reaction components, and such intermittent detection allows the damage to be avoided or at least delayed, thereby facilitating detection of the reaction at later stages. For example, if a detection method causes a reduction in processivity of a polymerase enzyme, then intermittent detection would allow data collection at noncontiguous regions of a template nucleic acid that extend farther from the initial binding site of the polymerase on the template than would be achievable under constant detection. Further, some detection methods have limits on how much data or for how long a time data may be generated in a single reaction, and intermittent detection of such a reaction can allow this data to be collected from various stages of a reaction, thereby increasing the flexibility of the investigator to spread out the data collection over multiple stages of a reaction. In certain aspects, the present invention is particularly suitable to characterization of analytical reactions in real time, that is, during the course of the reaction. In certain aspects, the present invention is particularly suitable to characterization of single molecules or molecular complexes monitored in analytical reactions, for example, single enzymes, nucleotides, polynucleotides, and complexes thereof.

In certain aspects, the present invention is directed to methods, devices, and systems for obtaining sequence data from discontiguous portions of single nucleic acid templates. The methods generally comprise providing a monitorable sequencing reaction comprising a polymerase, template, and primer sequence, as well as the various types of nucleotides or nucleotide analogs that are to be incorporated by the polymerase enzyme in the template-directed primer extension reaction. Typically, at least one or more or all of the nucleotides or nucleotide analogs are embodied with a detectable property that permits their identification upon or following incorporation. In the context of the present invention, the sequence data for a first portion of a template nucleic acid is acquired during a first stage of the reaction under a first set of reaction conditions that includes at least one reaction condition that results in degraded performance of the reaction, but that may contribute to the detectability of the nucleotides being incorporated. During a second stage of the reaction, the degradative influence is eliminated or reduced, which may result in an inability or a reduced ability to obtain sequence data from a second portion of the template nucleic acid, but where the second portion of the template nucleic acid is contiguous with the first portion. Subsequently, the reaction condition resulting in degraded performance is reinstated and sequence data is obtained for a third portion of the template nucleic acid during a third stage of the reaction, but where the third portion of the sequence is not contiguous with the first portion of the sequence, but is contiguous with the second portion.

The elimination or reduction of the degradative influence during the second stage of the reaction may be accomplished by changing or shortening one or more reaction conditions underlying degradative reaction performance, e.g., by changing one or more reaction conditions (e.g., temperature, pH, exposure to radiation, physical manipulation, etc.), and in particular may involve altering a reaction condition related to detection of one or more aspects or products of the reaction. For example, such an alteration in reaction conditions during the second stage may result in an increase in reaction rates, e.g., speeding up the progression of a template nucleic acid through a nanopore; or may reduce exposure of reaction components to harmful radiation or other reaction condition related to detection of the products of the reaction. However, in preferred embodiments, nucleotides or nucleotide analogs having the detectable property are present in the reaction mixture during all stages of the reaction, including stages in which the degradative influence is eliminated or reduced; as such, the reaction condition changed in stage two of such an embodiment would not comprise removal or dilution of such detectable nucleotides or nucleotide analogs.

"Intermittent detection," as used herein, generally refers to a means of monitoring a reaction that is carried out intermittently during the course of the reaction. Intermittent detection may refer to intermittent use of one or more monitoring methods, but does not necessarily mean that all means of monitoring a given reaction are intermittently halted. For example, monitoring of nucleotide incorporation to generate nucleotide sequence reads may be intermittently halted while other aspects of a sequencing reaction are constantly monitored, e.g., temperature, reaction time, pH, etc. In certain embodiments, intermittent detection is achieved by intermittent illumination of a given reaction, e.g., a reaction that uses an illumination system to detect reaction products or progression. Although various aspects of the invention are described herein in terms of embodiments using intermittent illumination, it should be understood that where applicable intermittent detection by other means (e.g., electrochemical, radiochemical, etc.) can be utilized in the methods of the invention. Likewise, a stage of a reaction during which an intermittent detection method is active may be referred to as a "detection period" and a stage of a reaction during which an intermittent detection method is inactive may be referred to as a "non-detection period." In illuminated reactions, such periods may also be referred to as "illuminated periods" and "non-illuminated periods," respectively.

In certain aspects, the present invention is generally directed to improved methods, devices, and systems for performing illuminated reactions. The term "illuminated reactions" as used herein refers to reactions which are exposed to an optical energy source. Typically, such illumination is provided in order to observe the generation and/or consumption of reactants or products that possess a particular optical characteristic indicative of their presence, such as a shift in the absorbance spectrum and/or emission spectrum of the reaction mixture or its components. In certain preferred embodiments, illuminated reactions comprise one or more fluorogenic or fluorescent components. In accordance with certain methods of the invention, such illuminated analyses are subjected to intermittent detection (e.g., data collection) for one or more aspects of the data typically collected for a given reaction. For example, aspects of the data typically collected for nucleotide sequencing reactions include nucleotide sequence data, read quality data, signal to background ratios, reaction rates and durations, measures of the fidelity of the reaction, reaction times, and the like. In certain preferred embodiments, nucleotide sequence data is iteratively collected during an ongoing sequencing reaction to generate nucleotide sequence reads for at least two or more noncontiguous regions of a template nucleic acid molecule. Such iterative sequence data acquisition may be achieved in various ways depending on the sequencing technology in use. For example, in sequencing methods that utilize luminescent components that generate a signal indicative of the identity of a base position, iterative sequence data collection may be achieved by removing or altering an illumination source (or a reaction relative to an illumination source), substituting the luminescent components for unlabeled components that do not generate signal, or otherwise interrupting signal acquisition in the experimental system.

In certain preferred embodiments, such illuminated reactions are illuminated for an amount of time that permits the effective performance of the analysis. Traditionally, illuminated reactions are illuminated from initiation through completion, and the time during which reaction data may be reliably collected is dictated by the progression (as measured by, e.g., processivity, rate, fidelity, duration, etc.) of the reaction under constant illumination. Some reactions are sensitive to such constant illumination, which can reduce their performance (e.g., processivity), and thereby prevent collection of data from later stages of the reaction, i.e., stages that would otherwise occur if the reaction were carried out with no illumination. The present invention provides methods for performing illuminated reactions comprising subjecting the reactions to intermittent illumination. Such intermittent illumination can increase performance (e.g., processivity, rate, fidelity, duration, etc.) of the reactions, thereby allowing generation of data that cannot be collected under constant illumination, such as data from later stages of an ongoing reaction whose progression is compromised under constant illumination. For example, in sequencing-by-incorporation reactions the use of intermittent excitation illumination can increase processivity, which has the benefit of providing sequence reads more distal from the polymerase binding/initiation site than such reactions subjected to constant exposure to excitation illumination.

Further, it is an object of the instant invention to provide sequence data from noncontiguous regions of a nucleic acid template in a single reaction. Other commercially available platforms have attempted to achieve such noncontiguous sequence data through, e.g., complex cloning and sequencing strategies. The present invention provides a clear advantage over such strategies by providing a simple and economical solution that is applicable across various platforms, and is particularly applicable to illuminated, single-molecule sequencing-by-incorporation reactions.

In preferred embodiments, illuminated reactions for use with the instant invention are nucleic acid sequencing reactions, e.g., sequencing-by-incorporation reactions. In preferred embodiments, such an illuminated reaction analyzes a single molecule to generate nucleotide sequence data pertaining to that single molecule. For example, a single nucleic acid template may be subjected to a sequencing-by-incorporation reaction to generate one or more sequence reads corresponding to the nucleotide sequence of the nucleic acid template. For a detailed discussion of such single molecule sequencing, see, e.g., U.S. Pat. Nos. 6,056,661, 6,917,726, 7,033,764, 7,052,847, 7,056,676, 7,170,050, 7,361,466, 7,416,844; Published U.S. Patent Application Nos. 2007-0134128 and 2003/0044781; and M. J. Levene, J. Korlach, S. W. Turner, M. Foquet, H. G. Craighead, W. W. Webb, SCIENCE 299:682-686, January 2003 Zero-Mode Waveguides for Single-Molecule Analysis at High Concentrations, all of which are incorporated herein by reference in their entireties for all purposes. In some embodiments, a plurality of single nucleic acid templates are analyzed separately and often simultaneously to generate a plurality of sequence reads corresponding to the nucleotide sequences of the plurality of nucleic acid templates. In certain preferred embodiments, the plurality of nucleic acid templates includes at least two nucleic acid templates that comprise identical nucleotide sequences such that analysis of the two nucleic acid templates generates overlapping sequence reads. In certain preferred embodiments, at least one of the nucleic acid templates is configured to provide redundant sequence data in a single sequence read, e.g., via duplications, sense and antisense sequences, and/or circularization.

Certain aspects of the invention are directed to methods, devices, and systems for generating a sequence scaffold for a nucleic acid template, e.g., chromosome, genome, or portion thereof. A sequence scaffold as used herein refers to a set of sequence reads that extends across at least a portion of a nucleic acid template. In some embodiments, such a sequence scaffold is used to generate a consensus sequence for the nucleic acid template. In some embodiments, the nucleic acid template is very large, e.g., at least about 100, 1000, 10,000, 100,000, or more bases or base pairs in length. In some embodiments, the sequence scaffold and/or consensus sequence is based on at least 1-, 2-, 5-, 10-, 20-, 50-, 100-, 200-, 500-, or 1000-fold coverage of at least a portion of the nucleic acid template. In some preferred embodiments, the portion of the nucleic acid is at least about 10%, 20%, 30%, 40%, 50%, 60%, 70%, 80%, 90%, or 100% of the entire length of the nucleic acid template.

In certain aspects, the invention is particularly suitable for sequencing nucleic acid templates interspersed with repetitive elements. Such repetitive elements present major logistical and computational difficulties for assembling fragments produced by sequencing strategies, especially those with read-lengths that are too short to encompass unique reads outside the repeat region. For example, the human T-cell receptor locus contains a five-fold repeat of a trypsinogen gene that is 4 kbp long and that varies 3 to 5% between copies. Therefore, a sequencing strategy that cannot provide nucleotide sequence information that spans at least 20 kb for a single molecule containing the locus will have difficulty providing consensus sequence for the locus. Further, Alu repeats (~300 bp retrotransposons) are also problematic because they cluster and can constitute up to 50-60% of the template sequence, with copies varying from 5-15% between each other. The human genome contains an estimated one million Alu repeats and 200,000 LINE elements (average length ~1000 bp), representing roughly 10% and 5% of the entire genome, respectively. In certain embodiments, the present methods facilitate efficient and accurate sequence determination for long templates comprising such repetitive sequences, in part because the present methods do not rely solely on sequence overlap to generate consensus sequences, but also include information related to the expected location of the polymerase on the template nucleic acid, thereby linking a particular sequence read to a particular location on the template nucleic acid. This greatly facilitates accurate assembly of sequence reads to generate sequence scaffolds and/or consensus sequences.

Certain aspects of the invention are directed to methods, devices, and systems for generating multiple sequence reads in an illuminated sequencing-by-incorporation reaction that are distal from one another (i.e., noncontiguous) on a single nucleic acid template by removing the excitation illumination during the course of the reaction, and subsequently reinitiating the excitation illumination. Sequence reads are generated only during the periods of time when the excitation illumination is present, resulting in a "gap" between the sequence reads from a single template nucleic acid that corresponds to the time during which the excitation illumination was absent but the incorporation of nascent nucleotides continued "in the dark." As such, the number of sequence reads generated for a given template nucleic acid is equal to the number of periods during which the excitation illumination is present.

Certain aspects of the invention are directed to methods, devices, and systems for generating multiple sequence reads from a plurality of nucleic acid templates comprising identical nucleotide sequences. In some embodiments, the multiple sequence reads are not all from the same region of the nucleic acid templates. In some embodiments, there is overlap between the multiple sequence reads. In some embodiments, a single sequence read is generated from each of the plurality of nucleic acid templates, and in other embodiments multiple noncontiguous sequence reads are generated from each of the plurality of nucleic acid templates. In certain preferred embodiments, the multiple noncontiguous sequence reads from each of the plurality of nucleic acid templates together extend across the nucleic acid templates such that they can be combined to provide a consensus sequence for the identical nucleotide sequence in the nucleic acid templates. In some embodiments, the consensus sequence is based on at least 2-, 5-, 10-, 20-, 50-, 100-, 200-, 500-, or 1000-fold coverage of the identical nucleotide sequence. In some embodiments, the identical nucleotide sequence represents at least about 10%, 20%, 30%, 40%, 50%, 60%, 70%, 80%, 90%, or 100% of the nucleic acid template.

Certain aspects of the invention are directed to methods, devices, and systems for reducing or limiting the effects of photo-induced damage during illuminated reactions, particularly reactions that employ fluorescent or fluorogenic reactants. The term "photo-induced damage" refers generally to any direct or indirect impact of illumination on one or more reagents in a reaction resulting in a negative impact upon that reaction. Without being bound to a particular theory or mechanism of operation, some illuminated reactions are subject to photo-induced damage that can hinder progression of the reaction, e.g., via damage to reaction components, such as enzymes, cofactors, templates, etc. As such, the illumination of the illuminated reaction can directly or indirectly negatively impact progression of the reaction, and such an impact can be measured based on various characteristics of the reaction progression, e.g., processivity, rate, fidelity, duration, etc. The present invention provides methods for subjecting an illuminated reaction to intermittent exposure to illumination, which reduces the amount of photo-induced damage at a given time during the reaction, allowing the reaction to proceed further than it does when constantly exposed to the illumination.

In some embodiments, the methods herein may further comprise the addition of one or more photo-induced damage mitigating agents (e.g., triplet-state quenchers and/or free radical quenchers) to the illuminated reaction. Such photodamage mitigating agents are generally known to those of skill in the art. Further discussion of photo-induced damage and related compounds, compositions, methods, devices, and systems are also provided in U.S. Pub. No. 20070161017, filed Dec. 1, 2006; and U.S. Ser. No. 61/116,048, filed Nov. 19, 2008, which are incorporated by reference herein in their entireties for all purposes.

II. INTERMITTENT ILLUMINATION OF ANALYTICAL REACTIONS

Certain aspects of the invention are generally directed to improved methods for performing illuminated analyses. The terms "illuminated analysis" and "illuminated reaction" are used interchangeably and generally refer to an analytical reaction that is occurring while being illuminated (e.g., with excitation radiation), so as to evaluate the production, consumption, and/or conversion of luminescent (e.g., fluorescent) reactants and/or products. As used herein, the terms "reactant" and "reagent" are used interchangeably. As used herein, the terms "excitation illumination" and "excitation radiation" are used interchangeably. In certain embodiments, the illuminated reaction is a sequencing reaction, e.g., a sequencing-by-incorporation reaction. In certain embodiments, the illuminated reaction is designed to analyze a single molecule, e.g., by ensuring the molecule is optically resolvable from any other molecule being analyzed and/or in the reaction mixture. In certain embodiments, one or more components of the reaction are susceptible to photo-induced damage directly or indirectly elicited by an excitation radiation source. In certain preferred embodiments, an illuminated reaction is subjected to intermittent excitation radiation during the course of the illuminated reaction. In certain preferred embodiments, a sequencing-by-incorporation reaction is subjected to intermittent excitation radiation during the course of a polymerization reaction to generate a plurality of noncontiguous sequence reads from a single nucleic acid template.

In certain aspects, the methods herein provide benefits over methods currently used for sequencing large template nucleic acids, such as human genomes. For example, the traditional shotgun sequencing approach entails sequencing nucleic acid fragments and analyzing the resulting sequence information for overlap and similarity to known sequences to construct the complete sequence of the template nucleic acid. One disadvantage to the shotgun approach is that assembly may be difficult if the template nucleic acid comprises numerous repeated sequences, and the inability to assemble a genomic sequence in repeat regions leads to gaps in the assembled sequence. (See, e.g., Myers, G.; "Whole-Genome DNA Sequencing" in *Computing in Science and Engineering*; Vol 1, Issue 3; pgs. 33-43; May/June 1999.) One method of resolving these gaps is to sequence fragments large enough to span the repeat regions, but sequencing large fragments can be difficult and time-consuming. Another approach to spanning a gap is to determine the sequence of two ends of a large fragment which has known spacing and orientation, and this approach is generally termed paired end sequencing (see, e.g., Smith, M. W. et al., (1994) Nature Genetics 7:40-47; and U.S. Pub. No. 2006/0292611, filed Jun. 6, 2006, both of which are incorporated by reference herein in their entireties for all purposes). This method is limited by the requirement for information about the spacing and orientation of the ends of the long fragment, and/or complex sample preparation of the nucleic acid template. The present invention provides methods that are tolerant of large repetitive regions and do not require prior knowledge of nucleotide sequences (e.g., base sequences, spacing, orientation, etc.) or complex sample preparation, thereby allowing economical, efficient, and effective de novo sequencing or resequencing of long template nucleic acids.

In certain aspects, the methods herein provide various strategies for achieving intermittent illumination of illuminated reactions. Essentially, the illumination (e.g., excitation illumination) is present for at least one time period ("illuminated period") and absent during at least one other time period ("non-illuminated period") during an illuminated reaction. The absence of the illumination may be due to, e.g., inactivation of the illumination source (e.g., laser, laser diode, a light-emitting diode (LED), a ultra-violet light bulb, and/or a white light source), removal of the illuminated reaction from the illumination source (or vice versa), or may be due to blockage of the illumination from the reaction, as discussed below. Knowledge of the rate of the reaction and the time during which the illumination is absent is used to estimate the progress of the reaction during the non-illuminated period. For example, if a reaction proceeds such that one molecule is incorporated into a macromolecule per second, and the illumination is absent for 20 seconds, it can be estimated that 20 molecules were incorporated during the non-illuminated period. This information is useful during data analysis to provide context for the reaction data collected during the illuminated period(s). For example, in a sequencing-by-incorporation reaction the number of base positions separating sequence reads generated in illuminated periods can be estimated based on the temporal length of intervening non-illuminated periods and the known rate of incorporation during the reaction and/or by the measured rate of incorporation during the illuminated period(s). This information is useful for positioning the sequence reads for a single template nucleic acid relative to one another in the construction of a sequence scaffold and/or consensus sequence for the template nucleic acid.

FIG. 1 provides exemplary embodiments of methods for intermittent illumination of analytical reactions. A reaction mix is prepared at step 100. In process A shown on the left, illumination of the reaction 105 is begun prior to initiation of the reaction 110, which allows "illumination data" to be collected at initiation. (In an alternative embodiment, illumination may commence simultaneously with initiation of the reaction.) "Illumination data" as used herein refers to data collected during an illuminated period, e.g., the length of the illuminated period and luminescent signal(s) from the reaction product. At least one non-illuminated period 115 occurs during the course of the reaction, followed by at least one additional illuminated period 120. Multiple additional non-illuminated and illuminated periods may follow. During the illuminated periods (105 and 120), illumination data is collected 175. During the non-illuminated period(s), non-illumination data is collected 180. As used herein, "non-illumination data" refers to data collected during a non-illuminated period, e.g., the length of the non-illuminated period can be monitored. In process B shown on the right, the reaction is initiated 155 during a first non-illuminated period 150. At least one illuminated period 160 occurs during the course of the reaction, optionally followed by at least one additional non-illuminated period 165. Multiple additional illuminated and non-illuminated periods may follow. As for process A, illumination data is collected 175 during the illuminated period(s) 160, and non-illumination data is collected 180 during non-illumination periods (155 and 165).

One benefit provided in certain embodiments of the invention is that the reaction need not be further manipulated after initiation (aside from the control of illumination). For example, the method can be used to analyze reaction mixtures without the need for buffer changes, addition of further reaction components, or removal of detectable components, e.g., light-activatable components such as fluorophores. For example, in a sequencing-by-incorporation reaction, labeled nucleotides may be present throughout the life of the reaction, even when the reaction is not generating nucleotide sequence data (e.g., during a non-illuminated period). This provides clear advantages over methods that require additional handling of the reaction after initiation, which tend to not only be expensive and time-consuming, but which also provide opportunities for contamination of the reaction. For example, illumination can be reinitiated at any time during the reaction at the whim of the ordinary practitioner by simply activating the illumination. In certain preferred embodiments, the concentration of labeled nucleotides or nucleotide analogs in the reaction mixture is greater than the concentration of unlabeled nucleotides in the reaction mixture throughout the course of the reactions, and may represent at least about 60%, 70%, 80%, 90%, 95%, 99%, or 100% of the total nucleotides in the reaction mixture. Methods for ensuring a high ratio of labeled versus unlabeled nucleotides in a reaction mixture are known in the art and certain preferred embodiments are provided in U.S. Patent Pub. Nos. 2006/0063264, 2006/0194232, and 2007/0141598, which are incorporated herein by reference in their entireties for all purposes.

In embodiments in which a sequencing-by-incorporation reaction is subjected to intermittent illumination, the sequence reads collected during the illuminated periods are arranged in order and separated from one another by an estimated number of nucleotides incorporated into the nascent strand during the intervening non-illuminated periods. The resulting gapped read can then be used to assess certain characteristics of the template nucleic acid. When multiple identical template nucleic acids are subjected to such a sequencing-by-incorporation reaction, the resulting set of gapped reads can be combined to create a sequence scaffold and/or a consensus sequence for the template nucleic acid.

Additional methods may also be used to aid in assembly of gapped reads into a sequence scaffold and/or a consensus sequence for a template nucleic acid. For example, in some embodiments, alternative labeling methods can be used to provide additional data during the course of the reaction, e.g., data from illuminated or non-illuminated periods. In certain preferred embodiments, such alternative labeling methods may comprise using labels that are incorporated into a product of the reaction. For example, in sequencing-by-incorporation reactions that use nucleotides comprising labeled terminal phosphates (e.g., the gamma phosphate as in dNTP, or terminal phosphates on nucleotide analogs with a greater number of phosphate groups) to identify the nucleotides incorporated into a nascent polynucleotide, the reaction mixture may also include nucleotides comprising a base-linked label. During the reaction, these "base-labeled nucleotides" will be incorporated into the nascent strand, but unlike the terminal phosphate labels removed during incorporation, the base-linked labels are not cleaved from the nucleotide upon incorporation by the polymerase, resulting in a nascent strand that comprises the base-linked labels. The concentration of such base-labeled nucleotides can be adjusted in the reaction mixture to promote their incorporation into the nascent strand at a predictable rate, e.g., based on the known sequence of the template or the average frequency of a given nucleotide. The presence and/or rate of incorporation of the base-linked labels into the nascent strand can provide a measure of the length of the nascent strand generated (and, therefore, the distance traveled by the polymerase along the template nucleic acid) during the reaction by subjecting the reaction to excitation illumination that excites the base-linked label (but preferably not the non-base-linked labels), and detecting the signal emitted. The excitation of the base-linked labels preferably occurs as a pulse during or immediately following a non-illuminated period, and is otherwise absent during the reaction. The strength of the signal is indicative of how many labels are present in the nascent strand, thereby providing a measure of the processivity of the polymerase for a given period during the ongoing reaction, e.g. during one or more illuminated or non-illuminated periods. Since the base-linked labels remain in the nascent strand, it is beneficial to minimize the amount of time those fluorophores are subjected to excitation illumination to mitigate the potential of photo-induced damage to the reaction components. As such, in preferred embodiments, the excitation illumination wavelength for the base-labeled nucleotides is different than that of other fluorescent labels in the reaction.

This method can be modified in various ways. For example, the base-labeled nucleotides may also comprise a terminal phosphate label so that their incorporation can be monitored in the same manner during an illuminated period as the non-base-labeled nucleotides. There may be a single type of base-labeled nucleotide in a reaction mixture, or multiple types may be present, e.g., each type carrying a different nucleobase. The concentration of base-labeled nucleotides in the reaction mix may be varied, although it is preferred that the ratio of base-labeled nucleotides to non-base-labeled nucleotides be relatively low. For example, in a reaction mixture comprising a single type of base-labeled nucleotide (e.g., base-labeled dATP), it is preferred that the ratio of base-labeled dATP to non-base labeled dATP be less than 1:8, and more preferably 1:10 or less. The low concentration of base-labeled nucleotides is preferred in order to minimize sterically induced polymerase stalling when incorporating multiple base-labeled nucleotides in a row. In some embodiments, the optimal ratio is pre-determined using capillary electrophoresis for any specific base-labeled nucleotide and likely homopolymer sequence prevalence. In certain preferred embodiments, at least 50, 75, 100, 125, or 150 base-labeled nucleotides are incorporated into the nascent strand during a single non-detection period. The base-labeled nucleotides may be present throughout the reaction, or may be washed in during non-illuminated periods and washed out after the pulse of excitation illumination. The reaction mixture comprising base-linked nucleotides being washed in may also include unlabeled nucleotides for incorporation during a non-detection period. During a subsequent illuminated period, a reaction mixture comprising terminal phosphate-labeled nucleotides replaces the reaction mixture comprising base-linked nucleotides and unlabeled nucleotides. This protocol is one embodiment of the methods of the invention in which a non-detection period is not necessarily a non-illuminated period because in this case illumination may be present, but no incorporation of nucleotides is be detected.

A given reaction may experience one or a plurality of illuminated periods or non-illuminated periods, but preferably experiences at least two illuminated periods. For example, a given reaction providing nucleotide sequence information from a single template nucleic acid may have at least about 2, 3, 5, 10, 20, 50, or 100 illuminated periods with intervening non-illuminated periods. In an embodiment employing multiple periods of illumination and/or non-illumination, the periods may be the same for both, e.g., 100 seconds "on" and 100 seconds "off." Alternatively, the illuminated periods may be longer or shorter than the non-illuminated periods. For example, in certain embodiments, a non-illuminated period may be at least about 2-, 3-, 4-, 6-, 8-, 10-, 20-, or 50-fold longer than an adjacent illuminated period; or an illuminated period may be at least about 2-, 3-, 4-, 6-, 8-, 10-, 20-, or 50-fold longer than an adjacent non-illuminated period. Further, each illuminated period may be the same or different from each other illuminated period, and each non-illuminated period may be the same or different from each other non-illuminated period. For example, some embodiments generate a smaller number of long reads, and other embodiments generate a larger number of short reads. It will be understood that the number and length of the illuminated and non-illuminated periods is limited only by the experimental system in use and the data acquisition goals of the ordinary practitioner. In some embodiments, a nucleotide sequence read generated during a single illuminated period comprises at least about 20, 30, 40, 50, 75, 100, 1000, 10,000, 25,000, 50,000, or 100,000 adjacent nucleotide positions. In some embodiments, a region of a nucleic acid template processed during a non-illuminated period during a single reaction comprises at least about 20, 30, 40, 50, 75, 100, 1000, 10,000, 25,000, 50,000, or 100,000 adjacent nucleotide positions. In some embodiments, the set of nucleotide sequence reads generated during a single sequencing reaction comprising a plurality of illuminated periods comprises at least about 40, 60, 80, 100, 1000, 10,000, 25,000, 50,000, 100,000, 250,000, 500,000, or 1,000,000 nucleotide sequence positions from a single nucleic acid template. In some embodiments, a set of nucleotide sequence reads generated during a single sequencing reaction comprising a plurality of illuminated periods comprises multiple reads of at least a portion of the nucleotide sequence positions from a single nucleic acid template.

As noted above, the present invention provides methods that are tolerant of large repetitive regions and do not require prior knowledge of nucleotide sequences (e.g., base sequences, spacing, orientation, etc.). However, such information, if available, may also be useful to the ordinary practitioner in determining an optimal periodicity for illuminated and non-illuminated periods during a sequencing reaction, especially when sequencing repetitive sequences. For example, if a genomic region is known to contain five adjacent copies of a one kilobase nucleotide sequence (i.e., five "repeat regions"), it would be beneficial to keep the non-illuminated periods short enough to be able to confidently map the resulting sequence reads to the correct repeat region. If a non-illuminated period were too long, the natural variation in translocation rate of the polymerase would make it difficult to assign a sequence read to a particular repeat region, especially those farther from the binding/initiation site of the polymerase. In a further example, if the "copies" each had a few mutations that could be used to distinguish them from each other, it would be beneficial to keep the illuminated periods long enough to increase the chance one of these mutations would be included in a resulting sequence read, thereby allowing the unambiguous assignment of the read to a particular repeat region. If the illuminated period were too short the sequence reads from two different repeat regions could be identical, making mapping the sequence read challenging. (Another way to mitigate these difficulties would be to incorporate pause or stop points into the template nucleic acid, as discussed below.)

Essentially, the practitioner may design the number of and lengths of time for each illuminated and non-illuminated period to best suit the illuminated reactions being analyzed and the invention is not limited in this regard. In certain embodiments, a practitioner may wish to increase the processivity of a polymerase thereby extending the length of the template nucleic acid processed in a sequencing reaction to be, e.g., at least 2-, 3-, 4-, 6-, 8-, 10-, or 20-fold, thereby generating sequence data much farther away from the polymerase binding/initiation site than would be achieved under constant illumination. In certain embodiments, a practitioner of the instant invention may wish to focus on data from one or more stages of an ongoing reaction, such as stages for which more data is required for analysis. In the case of sequencing-by-synthesis, one or more particular regions of a template nucleic acid may need to be resequenced. Some traditional methods require that new template nucleic acids be prepared to bring a region requiring resequencing closer to the initiation point of the sequencing reaction, or require preparation of multiple new templates if multiple regions to be resequenced. In contrast, the methods herein allow the practitioner to subject a template identical to the previously sequenced template (e.g., from a large genomic DNA sample preparation) to a sequencing reaction wherein illuminated periods are timed to illuminate the sample only when the polymerase is incorporating nucleotides into the nascent strand at the one or more particular regions requiring resequencing. This advantage substantially lowers the time and resources required for such resequencing operations, therefore providing a significant advantage over traditional methods.

The instant invention contemplates various means for providing non-illuminated periods during illuminated reactions. In some embodiments, the illumination source is turned off during the ongoing reaction to create one or more non-illuminated periods. In some embodiments, the illumination source remains on during the course of the reaction, but the illuminated reaction is removed from the system for a period of time. In some embodiments, the illumination source remains on during the course of the reaction, but the illumination is blocked to create one or more non-illuminated periods. For example, a movable mask may be manually or mechanically positioned between the illumination source and the illuminated reaction to block the illumination during non-illuminated periods and removed to allow exposure to the illumination during illuminated periods. Such a mask may also be dynamically controlled, such as a thin film transistor display (e.g., an LCD mask). Masks for blocking illumination and manufacture thereof are well known to those of ordinary skill in the art and need no further elaboration herein.

One aspect of the present invention is multiplexing of large numbers of single-molecule analyses. For a number of approaches, e.g., single molecule methods as described above, it may be desirable to provide the reaction components in individually optically resolvable configurations, such that a single reaction component or complex can be individually monitored. Providing such individually resolvable configurations can be accomplished through a number of mechanisms. For example, by providing a dilute solution of complexes on a substrate surface suited for immobilization, one will be able to provide individually optically resolvable complexes. (See, e.g., European Patent No. 1105529 to Balasubramanian, et al., the full disclosure of which is incorporated herein by reference in its entirety for all purposes.) Alternatively, one may provide a low density activated surface to which complexes are coupled. (See, e.g., Published International Patent Application No. WO 2007/041394, the full disclosure of which is incorporated herein by reference in its entirety for all purposes). Such individual complexes may be provided on planar substrates or otherwise incorporated into other structures, e.g., zero mode waveguides or waveguide arrays, to facilitate their observation.

In some embodiments, a plurality of illuminated reactions are carried out simultaneously, e.g., on a solid support. In some preferred embodiments, a solid support comprises an array of reaction sites. In preferred embodiments, the reaction sites on a solid support are optically resolvable from each other. In further preferred embodiments, each of the reaction sites on a solid support contains no more than a single reaction to be interrogated. For example, in a sequencing-by-incorporation embodiment, each reaction site preferably has no more than one polymerase and no more than one nucleic acid template. The reaction sites may be confinements (e.g., optical and/or physical confinements), each with an effective observation volume that permits resolution of individual molecules present at a concentration that is higher than one nanomolar, or higher than 100 nanomolar, or on the order of micromolar range. In certain preferred embodiments, each of the individual confinements yields an effective observation volume that permits resolution of individual molecules present at a physiologically relevant concentration, e.g., at a concentration higher than about 1 micromolar, or higher than 50 micromolar range or even higher than 100 micromolar. In addition, for purposes of discussion herein, whether a particular reagent is confined by virtue of structural barriers to its free movement, or is chemically tethered or immobilized to a surface of a substrate, it will be described as being "confined."

As used herein, a solid support may comprise any of a variety of formats, from planar substrates, e.g., glass slides or planar surfaces within a larger structure, e.g., a multi-well plates such as 96 well, 384 well and 1536 well plates or regularly spaced micro- or nano-porous substrates, or such substrates may comprise more irregular porous materials, such as membranes, aerogels, fibrous mats, or the like, or they may comprise particulate substrates, e.g., beads, spheres, metal or semiconductor nanoparticles, or the like. The solid support may comprise an array of one or more zero-mode waveguides or other nanoscale optical structures.

As used herein, "zero-mode waveguide" refers to an optical guide in which the majority of incident radiation is attenuated, preferably more than 80%, more preferably more than 90%, even more preferably more than 99% of the incident radiation is attenuated. As such high level of attenuation, no significant propagating modes of electromagnetic radiation exist in the guide. Consequently, the rapid decay of incident electromagnetic radiation at the entrance of such guide provides an extremely small observation volume effective to detect single molecules, even when they are present at a concentration as high as in the micromolar range. The fabrication and application of ZMWs in biochemical analysis, and methods for calling bases in sequencing-by-incorporation methods are described, e.g., in U.S. Pat. Nos. 7,315,019, 6,917,726, 7,013,054, 7,181,122, and 7,292,742, U.S. Patent Pub. No. 2003/0174992, and U.S. patent application Ser. No. 12/134,186, the full disclosures of which are incorporated herein by reference in their entirety for all purposes.

A set of reactions (e.g., contained on a solid support) may comprise identical or different components. For example, a single template nucleic acid may be analyzed in all reactions in the set, or a plurality of template nucleic acids may be analyzed, each present in only one or a subset of the set of reactions. In preferred embodiments, template nucleic acids comprising the same nucleotide sequence are analyzed in a plurality of reactions sufficient to provide adequate redundant nucleotide sequence data to determine a consensus sequence for the template nucleic acids. A number of sequence reads that will provide adequate nucleotide sequence data will vary, depending, e.g., on the quality of the template nucleic acid and other components of the reaction, but in general coverage for a template nucleic acid or portion(s) thereof is at least about 2-, 5-, 10-, 20-, 50-, 100-, 200-, 500-, or 1000-fold coverage. Further, the numbers and lengths of illuminated and non-illuminated periods for a given reaction in the set of reactions may be the same or different than those for other reactions in the set. In some embodiments, a mixture of different periodicities are used for a set of reactions comprising the same template nucleic acid. This strategy can be beneficial for providing nucleotide sequence reads from varying regions of the template sequence, thereby increasing the likelihood of overlapping sequence reads between individual reactions. These overlapping sequence reads can facilitate construction of a more robust sequence scaffold than could be constructed were the reactions all subjected to the same periodicity of illuminated and non-illuminated periods.

Methods of controlling polymerase progress and/or synchronizing polymerases in different reactions are also useful in analysis (e.g., mapping, validation, etc.) of nucleic acid reads farther from the initial binding site of the polymerase. During detection periods earlier in the reaction (i.e., closer to the time at which the polymerase began to process the template nucleic acid, such as during a first illuminated period), the position of a polymerase on the template can be estimated with generally good accuracy based on the known translocation rate of the polymerase under a given set of reaction conditions. As the duration of the reaction increases, however, the natural variation in polymerase translocation rate makes it more difficult to accurately determine the exact position of the polymerase on a template using estimation based on translocation rate alone; and through each subsequent illuminated period such estimations of polymerase position become less accurate, making subsequent analysis and mapping of the sequence reads to the template more difficult. Methods of regulating the position of the polymerase on the template allow more accurate determinations the polymerase's position. For example, causing the polymerase to pause or stop at a given location on the template during a non-illuminated period and reinitiating the polymerization during or immediately prior to a subsequent illuminated period provides a way to reorient the subsequently generated read with the template sequence, allowing easier consensus sequence determination and mapping analyses. Further, such pause/stop points can provide a means of controlling what regions of the template are processed during the illuminated periods by restricting where the polymerase will reinitiate on the template, thereby allowing a practioner of the instant invention to target one or more particular regions of a template for analysis during one or more detection periods during the course of an analytical reaction. Such methods are also useful to synchronize a set reactions being monitored simultaneously. For example, a plurality of reactions, each comprising a single polymerase/template complex, may be synchronized by regulating the initiation points of the polymerase on the template for each detection period, thereby creating a set of sequence reads that show less spreading (i.e., less variation in the position on the template from which the sequence reads are generated) in the later stages of the reactions than would otherwise be observed without such regulation.

Various methods can be used to control or monitor the progress of a polymerase on a template nucleic acid. For example, as noted above, one may employ a reaction stop or pause point within the template sequence, such as a reversibly bound blocking group at one location on the template, e.g., on the single-stranded portion that was not used in priming. By way of example, at a selected time following initiation of polymerization the reaction may be subjected to a non-illuminated period. The incorporation of a synthesis blocking group coupled to the template nucleic acid at a position encountered by the polymerase during the non-illuminated period will cause the polymerase to pause. An example of an engineered pause point is a known sequence on the template nucleic acid where a primer sits and blocks progression of a polymerase that is actively synthesizing a complementary strand. The presence of the primer by itself could introduce a pause in the polymerase sequencing or the primer could be chemically modified to force a full stop (and synchronization of multiple polymerases in multiple reactions). The chemical modification could be subsequently removed (for example, photo-chemically) and the polymerase would subsequently continue along the template nucleic acid. In some embodiments, multiple primers could be included in a reaction to introduce multiple pause or stop points along the template nucleic acid. Other methods for inducing a reversible pause (stop) in synthesis are known in the art and include, e.g., reversible sequestering of required cofactors (e.g., $Mn^{2+}$, one or more nucleotides, etc.). Once sufficient time has passed that the polymerase is paused at the blocking group, illumination is reintroduced and the blocking group removed. This allows control of the position on the template nucleic acid at which the polymerase will begin generating nucleotide sequence data during the illuminated period. A variety of synthesis controlling groups may be employed, including, e.g., large photolabile groups coupled to the template nucleic acid that inhibit polymerase mediated replication, strand-binding moieties that prevent processive synthesis, non-native nucleotides included within the primer and/or the template, and the like. Such reaction stops/pause points are useful in providing more certainty about the relationship of the reads to each other. For example, since the exact position on a template nucleic acid at which each sequence read begins would be known, the resulting reads could be better mapped relative to one another for construction of a sequence scaffold and/or consensus sequence. Further description of these and other methods for regulating the progress of a polymerase on a template are provided, e.g., in U.S. Ser. No. 61/099,696, U.S. Patent Pub. No. 2006/0160113, and U.S. Patent Pub. No. 2008/0009007, all of which are incorporated by reference herein in their entireties for all purposes.)

By way of example, a sequencing reaction may be initiated on a template comprising a non-native base in the absence of the complement to the non-native base, which would not impact the overall sequence determination of other portions of the template that are complementary to native bases. By starving the reaction for the complement to the non-native base, one can prohibit synthesis, and thus, the sequencing process, until the non-native base complement is added to the mixture. This can provide a "hot start" capability for the system and/or an internal check on the sequencing process and progress that is configurable to not interfere with sequence analysis of the regions of interest in the template, which would be complementary to only native bases. In some embodiments, the non-native base complement in the sequence mixture is provided with a detectably different label than the complements to the four native bases in the sequence, and the production of incorporation-based signals associated with such labels provides an indication that the polymerase has initiated or reinitiated. Although described as the "non-native base" it will be appreciated that this may comprise a set of non-natural bases that can provide multiple control elements within the template structure. In certain embodiments, two different non-native bases are included within the template structure, but at different points, to regulate procession of the sequencing process, e.g., allowing controlled initiation and a controlled stop/start position later in the sequence, e.g., prior to a subsequent illuminated period. For example, the complement to the first non-native base can be added to initiate sequencing immediately prior to the start of a first illuminated period. During a first non-illuminated period following the first illuminated period, the polymerase encounters the second non-native base, e.g., at a nucleotide position near but upstream of a nucleotide region desired to be sequenced in a second illuminated period. Sequencing would stop until the complement to the second non-native base is added to the reaction mixture. Likewise, multiple such non-native bases could be incorporated into the template to effectively target the polymerase to multiple regions of interest for which sequence data is desired. Further, in applications in which multiple identical templates are being sequenced, this would allow a resynchronization of the various sequencing reactions and the data generated therefrom.

Figure 2:
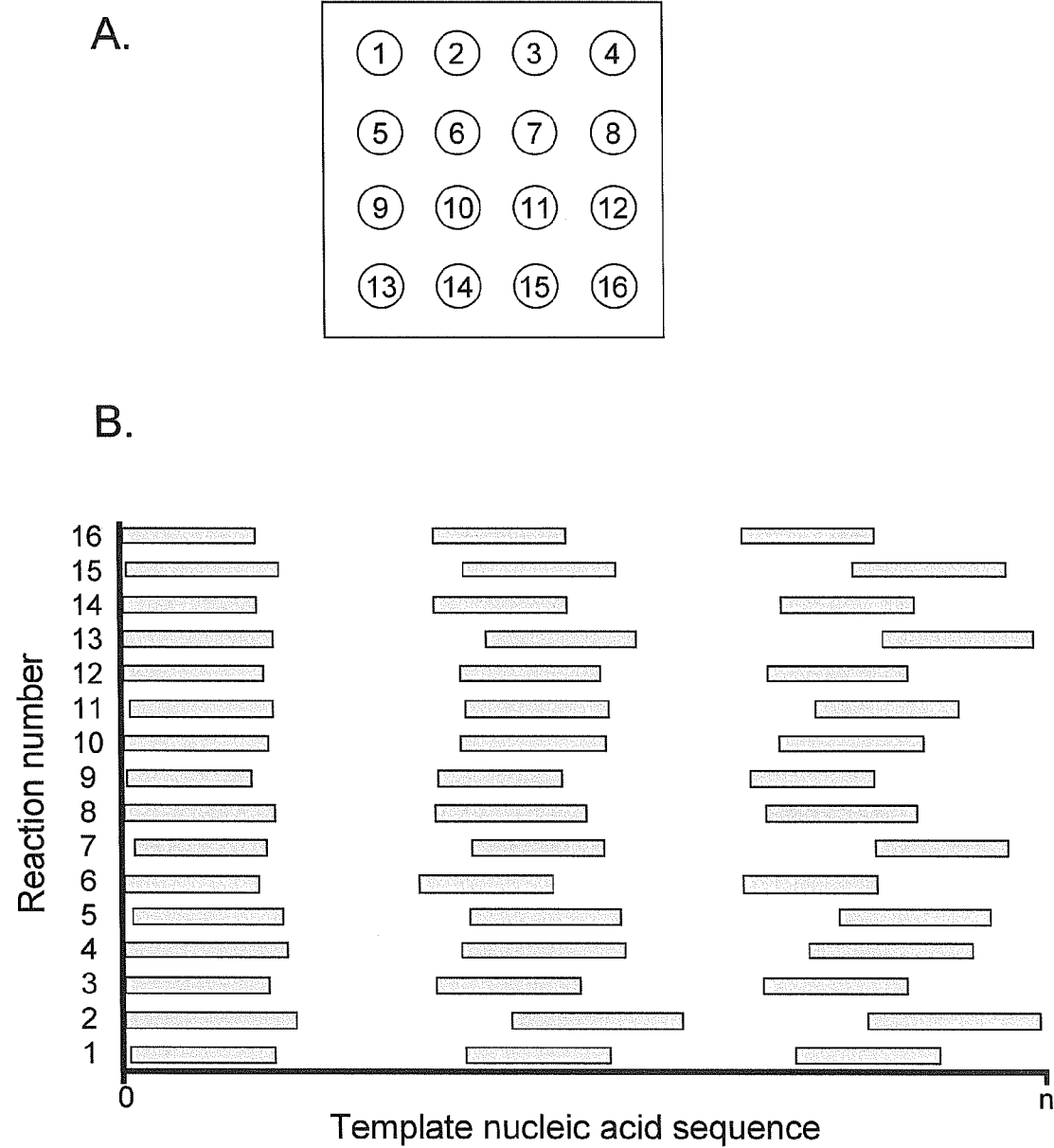
FIG. 2 provides an exemplary embodiment of analysis of a plurality of illuminated reactions using intermittent illumination, including depictions of multiple reactions arrayed on a solid support (A) and prophetic data (B) from certain embodiments of the invention.

FIG. 2 provides an exemplary embodiment of analysis of a plurality of illuminated reactions using intermittent illumination. In this embodiment, sixteen sequencing-by-incorporation reactions are performed on single nucleic acid templates (each of which comprises the same nucleotide sequence) with the timing of the illuminated and non-illuminated periods the same for all sixteen reactions. In A, the sixteen reactions are shown disposed on sixteen reaction sites on a solid support and are numbered for convenience. A representation of the illumination data is shown in B, with bars extending across the graph indicative of illumination data collected during illuminated periods for each reaction. In this illustrative example, each reaction is subjected to three illuminated periods, each followed by a non-illuminated period, resulting in three noncontiguous sequence reads for each reaction, i.e., three noncontiguous reads per template molecule sequenced. The position of the bars relative to the x-axis provides the position of the sequence read relative to the template nucleic acid sequence, which extends from position 0 (initiation of sequencing reaction) to n. During the first illuminated period, the sequence reads generally overlap, but the natural variation of polymerase translocation rate over the set of reactions results in a "spreading" of the sequence reads as the reaction proceeds through the second and third illuminated periods with increasing variation in the exact position of each polymerase on the template at the beginning and end of each illuminated period. As such, the earlier illumination data provides better redundancy ("oversampling") of sequence information over a relatively narrow portion of the template nucleic acid, while the later illumination periods provide less redundant sequencing data over a broader region of the template nucleic acid. The timing of the non-illuminated periods between the illuminated periods and the known or calculated rate of incorporation are used to determine approximate spacing between the resulting sequence reads, providing context for building a sequence scaffold or consensus sequence. It is important to note that although shown disposed on a solid support in A, the data shown in B could also have been generated from reactions not disposed on a solid support nor performed simultaneously and the methods are generally not so limited. Further, as described above, the spreading of the sequence reads from later stages of the reactions can be mitigated by synchronizing the reactions, e.g., by regulating the initiation points of the polymerase on the template for each detection period, thereby creating a set of sequence reads that provides better redundancy (i.e., more overlap in the positions on the template from which the sequence reads are generated), especially in the later stages of the reactions.

Using templates that allow repeated sequencing (e.g., circular templates) in a single reaction can increase the percent of a nucleic acid template for which nucleotide sequence data is generated, thereby providing more complete data for further analysis, e.g., construction of sequence scaffolds and/or consensus sequences for the nucleic acid template. For example, each time a circular template is sequenced the timing of the illuminated and non-illuminated periods can be reset to change the regions of the template for which nucleotide sequence data is generated. Alternatively, each time a circular template is sequenced the timing of the illuminated and non-illuminated periods can be kept the same to provide a greater-fold coverage of one or more regions of interest in the template. Various methods for generating redundant sequence reads are known in the art, and certain specific methods are provided in U.S. Pat. No. 7,302,146; U.S. Pat. No. 7,476,503; U.S. Ser. No. 61/094,837, filed Sep. 5, 2008; U.S. Ser. No. 61/099,696, filed Sep. 24, 2008; and U.S. Ser. No. 61/072,160, filed Mar. 28, 2008, all of which are incorporated by reference herein in their entireties for all purposes. A specific embodiment is also provided in the Exemplary Applications section herein.

Another exemplary embodiment of an analysis of a plurality of illuminated reactions using intermittent illumination comprises a first illuminated period that is initiated at different times over the plurality of reactions. For example, the illuminated period for a first reaction may start at 0 seconds, the illuminated period for a second reaction may start at 5 seconds, the illuminated period for a third reaction may start at 10 seconds, and so forth. Additionally or alternatively, a first subset of reactions may begin at a first time, a second subset may begin at a second time, etc. The first illumination period continues for a given length of time, followed by a non-illuminated period and a subsequent second illuminated period. Optionally, a plurality of non-illuminated periods and illuminated periods follow the first illuminated period. Staggered start times can provide staggered data sets (e.g., two or more sequence reads) for the plurality of reactions, allowing multiple different stages of the overall reaction to be interrogated in different reactions. Preferably, the staggered data sets overlap to an extent that allows further analysis and validation of the reaction data. For example, a sequencing-by-incorporation reaction subjected to such an embodiment of the invention would preferably have sufficient overlap between sequence reads from different individual reactions to allow construction of a sequence scaffold and/or consensus sequence for a template nucleic acid.

A mask for use with a solid support (e.g., an array of confinements) can be designed to allow illumination of one or more portions of the solid support while blocking illumination to other portions of the solid support. For example, a mask may comprise one or more windows that allow excitation illumination to pass through the mask. Such a mask may be physically moved over the surface of the solid support (or the solid support can be moved relative to the mask), e.g., to selectively allow excitation illumination to reach a subset of confinements in an array. For example, a mask that allows 10% of reaction sites to be illuminated could be used to increase the sequencing scaffold coverage by sliding the illumination area (the area being subjected to excitation illumination) back and forth across the solid support. The 10% of reactions would cover certain regions of the nucleic acid template for any given time period (and therefore region of sequence in the template). In certain embodiments, an automated mask that selectively controls the timing of illumination of reactions on a solid support during the course of the reaction/acquisition may be used rather than a mask that must be physically moved.

Figure 4:
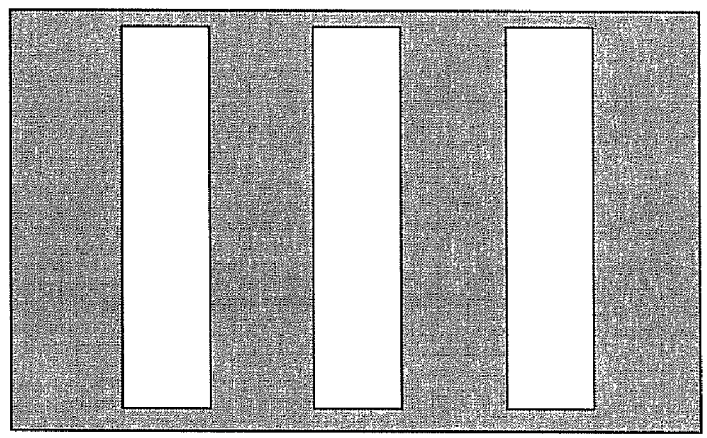
FIG. 4 provides additional embodiments of masks for use in the methods of the invention, including a mask that allows illumination of columns of reactions (A) and a mask that allows illumination of every other reaction in a row and column (B).
Figure 4:
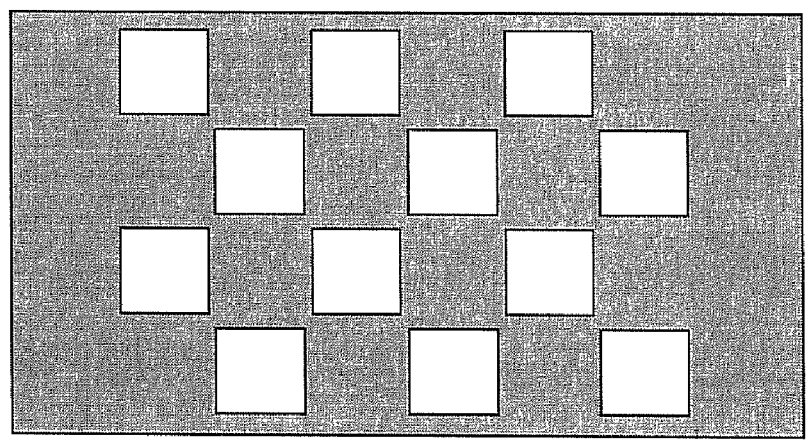
Figure 5:
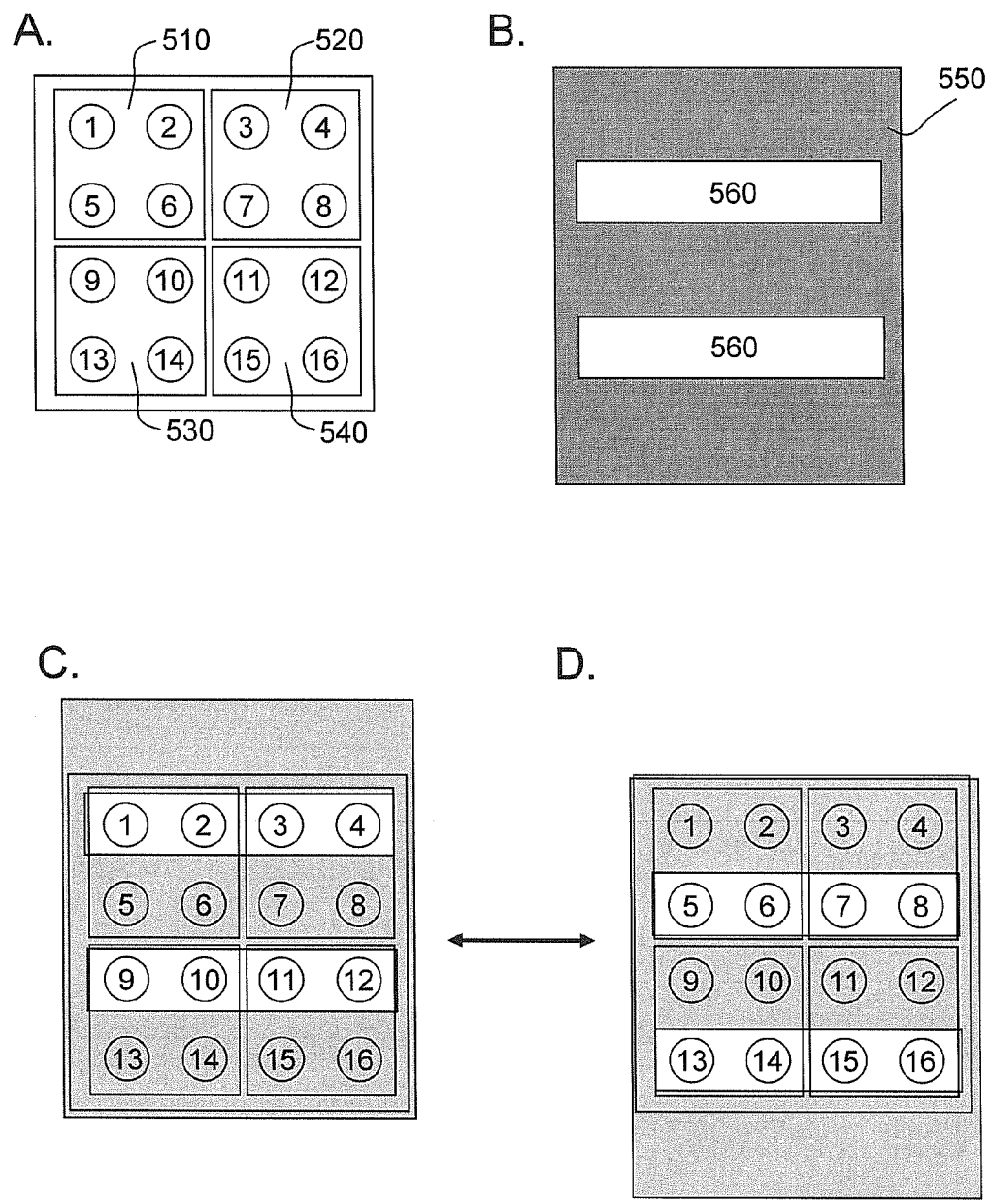
FIG. 5 illustrates an aspect of the instant invention in which multiple samples are analyzed on a single solid support using intermittent illumination.

The timing of the illuminated and non-illuminated periods for a set of reactions on a solid support may be the same or may vary, and may be synchronized or random. In certain embodiments in which the excitation illumination source is turned on and off, the timing of the illuminated and non-illuminated periods for the set of reactions will be identical. In other embodiments, for example, those that comprise use of a mask, the timing of the illuminated and non-illuminated periods for the set of reactions can vary so that while a subset of the reactions are illuminated, another subset of the reactions are not illuminated. Various exemplary and nonlimiting embodiments of masks that may be used with a set of reactions on a solid substrate are provided in FIGS. 3-5, as described below. In certain embodiments, the illuminated/non-illuminated status of each reaction may be random across the solid support, e.g., to remove any experimental bias potentially introduced by actively selecting which reactions to illuminate at a given time, as long as the sequence reads being generated at the illuminated reactions and the time at which these reactions are not illuminated are able to be assigned to a particular reaction. For ease of discussion, the action of both illuminating and collecting emission signals from a reaction of interest, or a particular region on a solid support in which a reaction of interest is taking place, is referred to as "interrogating" that reaction and/or that region. A region being so interrogated is termed an "observation region."

Figure 3:
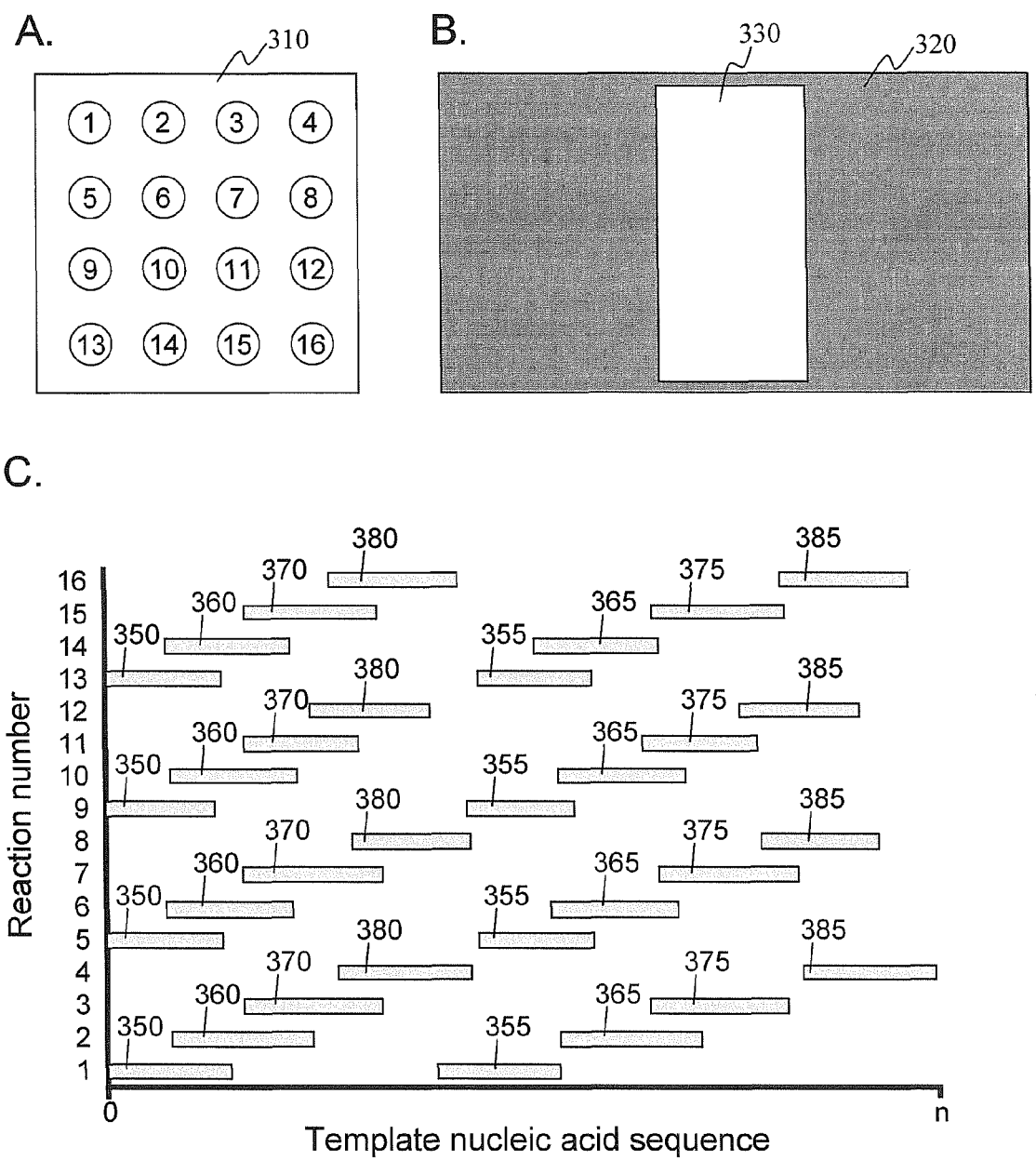
FIG. 3 provides an exemplary embodiment of analysis of a plurality of illuminated reactions on a solid support (A) using intermittent illumination and a mask (B). A graph (C) depicts prophetic data from certain embodiments of the invention.

FIG. 3 provides an exemplary embodiment of analysis of a plurality of illuminated reactions using intermittent illumination and a mask. As in FIG. 2, an array of reactions on a solid support 310 is provided containing sixteen reaction sites, numbered for convenience (A). In B, a mask 320 is provided with a single window 330 to allow passage of illumination to a subset of reactions on the solid support. Window 330 is wide enough to allow illumination of at least two columns of reaction sites on solid support 310. As in FIG. 2, a representation of the illumination data is shown in C, with bars extending across the graph indicative of illumination data collected for each reaction. The position of the bars relative to the x-axis provides the position of the sequence read relative to the template nucleic acid sequence, which extends from position 0 (initiation of sequencing reaction) to n. When the sequencing reaction is initiated at all positions on solid support 310, the window 330 is positioned to allow illumination to only reactions 1, 5, 9, and 13, and these four reactions provide sequence reads 350 for the earliest stage of the reactions. The window 330 is subsequently moved to provide an illuminated period for reactions 2, 6, 10, and 14 while still continuing the illumination period for reactions 1, 5, 9, and 13. The illumination data for reactions 2, 6, 10, and 14 provides sequence reads 360, which partially overlap sequence reads 350 for reactions 1, 5, 9, and 13. The window 330 is moved again to provide illuminated periods for reactions 3, 7, 11, and 15 while still continuing the illumination period for reactions 2, 6, 10, and 14, but removing illumination from reactions 1, 5, 9, and 13. The illumination data for 3, 7, 11, and 15 results in sequence reads 370, which partially overlap sequence reads 360 for reactions 2, 6, 10, and 14. A fourth position of the mask 320 initiates an illuminated period for reactions 4, 8, 12, and 16 while continuing illumination of reactions 3, 7, 11, and 15, but ending the illuminated period for reactions 2, 6, 10, and 14. Sequence reads 380 correspond to sequence reads from reactions 4, 8, 12, and 16. Finally, the window is moved to end the illuminated period for reactions 3, 7, 11, and 15 while continuing the illuminated period for reactions 4, 8, 12, and 16. Repeating the above process allows a second read to be generated from each reaction, and this second read is noncontiguous with the first read. For example, reactions 1, 5, 9, and 13 correspond to reads 350 and, later in the reaction, reads 355. The two reads generated in a single reaction do not overlap and are separated by a length of nucleotides that was incorporated during the non-illuminated period between the two illuminated periods.

The mask can optionally be passed over the substrate additional times to generate additional reads until the reactions are complete or no longer provide reliable data, such as when the total illumination time (computed by summing the times for the multiple illuminated periods) has surpassed a photo-induced damage threshold period. Further, the mask may be passed back and forth, or may pass over the solid support in only one direction, e.g., always left to right, or vice versa.

Further, unlike the data shown in FIG. 2B which has gaps in the sequence coverage for the template nucleic acid, the strategy provided in this embodiment results in at least two-fold coverage across the entire template nucleic acid (FIG. 3C), although at a lower-fold redundancy. The portion of the template covered by only reads 380 and reads 355 has the least-fold redundancy, and in some instances a gap in coverage may be present in this region due to the movement of the mask 320 from the far right to the far left of the solid support 310. Of course, oversampling by adding replicate reactions to the set of reactions, or using templates that allow repeated sequencing (e.g., circular templates) in a single reaction can increase the coverage of a nucleic acid template, thereby providing more data for construction of sequence scaffolds and/or consensus sequences for the nucleic acid template. Various methods for generating redundant sequence reads are known in the art, and certain specific methods are provided in U.S. Pat. No. 7,302,146; U.S. Pat. No. 7,476,503; U.S. Ser. No. 61/094,837, filed Sep. 5, 2008; U.S. Ser. No. 61/099,696, filed Sep. 24, 2008; and U.S. Ser. No. 61/072,160, filed Mar. 28, 2008, all of which have been previously incorporated by reference herein. The natural variation of polymerase translocation rate over the set of reactions is also apparent in this prophetic example as the spreading of the sequence reads and decreasing overlap between reads from reactions in adjacent columns in the later stages of the reactions as compared to the earlier stages.

FIG. 4A provides an embodiment of a mask similar to that provided in FIG. 3 except that it comprises three windows allowing multiple nonadjacent columns of reaction sites to be illuminated simultaneously. FIG. 4B provides an embodiment of a mask comprising twelve windows, each of which allows illumination of a single reaction site on a solid support. The windows are oriented in the mask to allow illumination of every other reaction in each row and every other reaction in each column. It will be understood that these mask designs are merely exemplary and nonlimiting embodiments as it is well within the abilities of the ordinary practitioner to determine an appropriate mask design depending on the experimental design or the illuminated reactions to be interrogated.

FIG. 5B illustrates yet another aspect of the instant invention in which multiple samples are analyzed on a single solid support using intermittent illumination. Four different samples are disposed on a solid support, one in each quadrant 510, 520, 530, and 540 (A). A mask 550 is used that comprises two windows 560 that allow multiple rows of reaction sites to be illuminated simultaneously (B). A first position of this mask over a solid support in which two reactions in each quadrant are illuminated is demonstrated in C. A second position of the mask allowing illumination of the previously non-illuminated reactions is demonstrated in D. The mask may be moved back and forth as indicated by the double-arrow to provide multiple illuminated and non-illuminated periods for each reaction containing one of the four samples.

The present invention is also useful for redundant interrogation of reactions or portions of a solid support of interest. In certain aspects, sequential interrogation of different observation regions may be repeated a number of times, e.g., more than 2, 5, 10, 50, 100, 500, 1000, or even more than 10,000 times. In general, this method of stepping the observation region to another, preferably adjacent region, and repeating the interrogation process is generally referred to as a "step and repeat" process, and may be performed by various methods, including but not limited to moving the incident light and the solid support relative to one another and moving a mask across the surface of the solid support, as described above. Although described as a "step and repeat" method, in some embodiments where the observation region is moved across a substrate, that movement is not step-wise and iterative, but instead constitutes a continuous motion, substantially continuous motion, or stepped movement, or an iterative motion whereby each iterative step interrogates a new region that overlaps with some portion of the previously interrogated region. In particular, a substrate may be moved continuously relative to an optical system, whereby the observation region moves continuously across the substrate being interrogated (in a "scan mode").

The present invention is optionally combined with an optical system that provides illumination and/or collection of emitted illumination. Preferably, the optical system is operatively coupled to the reaction sites, e.g., on a solid support. One example of a particularly preferred optical system is described in U.S. Ser. No. 11/201,768, filed Aug. 11, 2005, and incorporated herein by reference in its entirety for all purposes. Optical systems are described further below.

In some embodiments, one or both of the solid support and optical system are moved during interrogation. For example, a solid support being interrogated may be held stationary while the optical system is moved, or the solid support may be moved relative to a stationary optical system. Such movement may be accomplished using any of a variety of manipulation hardware or robotic set-ups, e.g., a stepper/feeder apparatus, and are well known in high performance printing technologies and in the semiconductor industry. For example, robotic systems may be used to pick up and re-orient a given solid support in order to interrogate different regions of the solid support, or make a previously unaccessible region (e.g., blocked by clips, support structure, or the like) of the solid support accessible. Such robotic systems are generally available from, e.g., Beckman, Inc., Tecan, Inc., Caliper Life Sciences, and the like.

In addition to the foregoing, it will be appreciated that the reagents in a given reaction of interest, including those reagents for which photo-induced damage is being mitigated in accordance with the invention, may be provided in any of a variety of different configurations. For example, they may be provided free in solution, or complexed with other materials, e.g., other reagents and/or solid supports. Likewise, such reagents may be provided coupled to beads, particles, nanocrystals or other nanoparticles, or they may be tethered to larger solid supports, such as matrices or planar surfaces. These reagents may be further coupled or complexed together with other reagents, or as separate reagent populations or even as individual molecules, e.g., that are detectably resolvable from other molecules within the reaction space. As noted above, whether a particular reagent is confined by virtue of structural barriers to its free movement or is chemically tethered or immobilized to a surface of a substrate, it will be described as being "confined." Further examples of such confined reagents include surface immobilized or localized reagents, e.g., surface immobilized or associated enzymes, antibodies, etc. that are interrogated upon the surface, e.g., through fluorescence scanning microscopy or scanning confocal microscopy, total internal reflection microscopy or fluorometry, microscopy utilizing evanescent waves (see, e.g., U.S. Patent Publication Nos. 20080128627, filed Aug. 31, 2007; 20080152281, filed Oct. 31, 2007; and 200801552280, filed Oct. 31, 2007, all of which are incorporated by reference in their entireties for all purposes), surface imaging, or the like. For example, in some preferred embodiments, one or more reagents in an assay system are confined within an optical confinement. Such an optical confinement may be an internal reflection confinement (IRC) or an external reflection confinement (ERC), a zero-mode waveguide, or an alternative optical structure, such as one comprising porous film with reflective index media or a confinement using index matching solids. More detailed descriptions of various types of optical confinements are provided, e.g., in International Application Publication No. WO/2006/083751, incorporated herein by reference in its entirety for all purposes.

The invention is generally applicable to any of a variety of optical assays that require substantial illumination and/or photoactivated conversion or excitation of chemical groups, e.g., fluorophores. For example, the compositions and methods provided herein may be used with fluorescence microscopy, optical traps and tweezers, spectrophotometry, fluorescence correlation spectroscopy, confocal microscopy, near-field optical methods, fluorescence resonance energy transfer (FRET), structured illumination microscopy, total internal reflection fluorescence microscopy (TIRF), etc. The methods provided herein may be particularly useful in assays that are negatively impacted, directly or indirectly, by prolonged exposure to illumination. Of particular interest are those assays that are impaired by the generation and/or accumulation of triplet-state forms or free radicals during illumination.

One particularly apt example of analyses that benefit from the invention are single-molecule biological analyses, including, inter alia, single molecule nucleic acid sequencing analyses, single molecule enzyme analyses, hybridization assays (e.g., antibody assays), nucleic acid hybridization assays, and the like, where the reagents of primary import are subjected to prolonged illumination with relatively concentrated light sources (e.g., lasers and other concentrated light sources, such as mercury, xenon, halogen, or other lamps) in an environment where photoconversion/excitation is occurring with its associated generation of products. In certain embodiments, the methods, compositions, and systems are used in nucleic acid sequencing processes that rely on detection of fluorescent or fluorogenic reagents. Examples of such sequencing technologies include, for example, SMRT™ nucleic acid sequencing (described in, e.g., U.S. Pat. Nos. 6,399,335, 6,056,661, 7,052,847, 7,033,764, 7,056,676, 7,361,466, 7,416,844, the full disclosures of which are incorporated herein by reference in their entirety for all purposes), non-real-time, or "one base at a time" sequencing methods available from, e.g., Illumina, Inc. (San Diego, Calif.), Helicos BioSciences (Cambridge, Mass.), Clonal Single Molecule Array™, and SOLiD™ sequencing. (See, e.g., Harris, et al. (2008) Science 320 (5872):106-9, incorporated by reference herein in its entirety for all purposes.) Such prolonged illumination can negatively impact (e.g., by introducing photo-induced damage) these reagents and diminish their effectiveness in the desired reaction.

III. PREVENTION OF PHOTO-INDUCED DAMAGE

The methods provided herein are particularly useful in analyses that utilize very limited concentrations of reactants, such as single molecule detection/monitoring assays. As will be appreciated, in such reagent limited analyses, any loss, degradation, or depletion of a critical reagent will dramatically impact the analysis by further limiting the reagent, which not only can adversely effect the detectable signal, but may also directly impact the reaction being monitored, e.g., by changing its rate, duration, or product(s). For example, photo-induced damage can include a photoinduced change in a given reagent that reduces the reactivity of that reagent in the reaction, e.g., photobleaching of a fluorescent molecule, which diminishes or removes its ability to act as a signaling molecule. Also included in the term photo-induced damage are other changes that reduce a reactant's usefulness in a reaction, e.g., by making the reagent less specific in its activity in the reaction. Likewise, photo-induced damage includes undesired changes in a reagent that are caused by interaction of that reagent with a product of another photoinduced reaction, e.g., the generation of singlet oxygen during a fluorescence excitation event, which singlet oxygen may damage organic or other reagents, e.g., proteins. Photo-induced damage also includes downstream effects of damage to reactants, such as irreversible interactions between damaged reactants and other critical components of the reaction, e.g., reactive proteins or enzymes. For example, damage to an enzyme that catalyzes a reaction being monitored may cause a reduction in the rate of the reaction, in some cases stopping it altogether, or may reduce the duration or fidelity of the reaction.

As suggested by the foregoing, photo-induced damage generally refers to an alteration in a given reagent, reactant, or the like, that causes such reagent to have altered functionality in a desired reaction, e.g., reduced activity, reduced specificity, or a reduced ability to be acted upon, converted, or modified, by another molecule, that results from, either directly or indirectly, a photo-induced reaction, e.g., a photo-induced reaction creates a reactant that interacts with and causes damage to one or more other reactants. Typically, such photoreaction directly impacts either the reactant of interest, e.g., direct photo-induced damage, or impacts a reactant within one, two or three reactive steps of such reactant of interest. Further, such photoreaction can directly impact the reaction of interest, e.g., causing a change in rate, duration, processivity, or fidelity of the reaction.

The amount of time an illuminated analysis may be carried out before photo-induced damage so substantially impacts the reactants to render the analysis non-useful is referred to as the "photo-induced damage threshold period." A photo-induced damage threshold period is assay-dependent, and is affected by various factors, including but not limited to characteristics of enzymes in the assay (e.g., susceptibility to photo-induced damage and the effect of such damage on enzyme activity/processivity), characteristics of the radiation source (e.g., wavelength, intensity), characteristics of the signal-generating molecule (e.g., type of emission, susceptibility to photo-induced damage, propensity to enter triplet state, and the effect of such damage on the brightness/duration of the signal), similar characteristics of other components of the assay. It can also depend on various components of the assay system, e.g., signal transmission and detection, data collection and analysis procedures, etc. It is well within the abilities of the ordinary practitioner to determine an acceptable photo-induced damage threshold period for a given assay, e.g., by monitoring the signal decay for the assay in the presence of a photodamaging agent and identifying a period for which the signal is a reliable measure for the assay. In terms of the invention, the photo-induced damage threshold period is that period of illuminated analysis during which such photo-induced damage occurs so as to reduce the rate or processivity of the subject reaction by at least 10%, 20%, 30%, 40%, 50%, 60%, 70%, 80%, or 90% over the same reaction in the absence of such illumination. It is an object of the invention to increase the photo-induced damage threshold period, thereby increasing the amount of time reactions can proceed toward completion with minimal damage to the reactants, thereby lengthening the time in which the detectable signal is an accurate measure of reaction progression.

In some contexts, a "photo-induced damaged" reaction may be subject to spurious activity, and thus be more active than desired. In such cases, it will be appreciated that the photo-induced damage threshold period of interest would be characterized by that period of illuminated analysis during which such spurious activity, e.g., as measured by an increase in reaction rate, or an increase in non-specific reaction rate, is no more than 10%, 20%, 30%, 40%, 50%, 60%, 70%, 80%, or 90% over a non-illuminated reaction. In one non-limiting example, where a nucleic acid polymerase, by virtue of a photodamaging event, begins to incorrectly incorporate nucleotides during template directed synthesis, such activity would impact the photo-induced damage threshold period as set forth above. In this case, the methods, devices, and systems of the invention would increase the photo-induced damage threshold period, thus increasing the amount of time the reaction could proceed before the above-described spurious activity occurred.

With reference to nucleic acid analyses, it has been observed that in template-directed synthesis of nucleic acids using fluorescent nucleotide analogs as a substrate, prolonged illumination can result in a substantial degradation in the ability of the polymerase to synthesize the nascent strand of DNA, as described previously, e.g., in U.S. Published Patent Application No. 20070161017, incorporated by reference herein in its entirety for all purposes. Damage to polymerase enzymes, template sequences, and/or primer sequences can significantly hinder the ability of the polymerase to process longer strands of nucleic acids. For example, reduction in the processivity of a polymerase leads to a reduction in read lengths for sequencing processes that identify sequence constituents based upon their incorporation into the nascent strand. As is appreciated in the art of genetic analysis, the length of contiguous reads of sequence directly impacts the ability to assemble genomic information from segments of genomic DNA. Such a reduction in the activity of an enzyme can have significant effects on many different kinds of reactions in addition to sequencing reactions, such as ligations, cleavages, digestions, phosphorylations, etc.

Without being bound to a particular theory or mechanism of operation, it is believed that at least one cause of photo-induced damage to enzyme activity, particularly in the presence of fluorescent reagents, results from the direct interaction of the enzyme with photo-induced damaged fluorescent reagents. Further, it is believed that this photo-induced damage of the fluorescent reagents (and possibly additional damage to the enzyme) is at least partially mediated by reactive intermediates (e.g., reactive oxygen species) that are generated during the relaxation of triplet-state fluorophores. One or both of the photo-induced damaged fluorescent reagents and/or reactive intermediates may be included in the overall detrimental effects of photo-induced damage.

In certain aspects, the invention is directed to methods, devices, and systems that reduce the amount of photo-induced damage to one or more reactants during an illuminated reaction, e.g., thereby improving the reaction, e.g., by increasing the processivity, rate, fidelity, processivity, or duration of the reaction. In particular, methods are provided that yield a reduction in the level of photo-induced damage and/or an increase in the photo-induced damage threshold period as compared to such reactions in the absence of such methods, devices, and systems. In particular embodiments, such methods comprise subjecting an illuminated reaction to periods of non-illumination during the course of the reaction, as described above, or by temporarily removing components of the reaction mixture that are believed to cause such damage, as described below.

As generally referred to herein, limited quantity reagents or reactants may be present in solution, but at very limited concentrations, e.g., less than 200 nM, in some cases less than 10 nM and in still other cases, less than 10 pM. In preferred aspects, however, such limited quantity reagents or reactants refer to reactants that are immobilized or otherwise confined within a given area or reaction site (e.g., a zero-mode waveguide), so as to provide limited quantity of reagents in that given area, and in certain cases, provide small numbers of molecules of such reagents within that given area, e.g., from 1 to 1000 individual molecules, preferably between 1 and 10 molecules. As will be appreciated, photo-induced damage of immobilized reactants in a given area will have a substantial impact on the reactivity of that area, as other, non-damaged reactants are not free to diffuse into and mask the effects of such damage. Examples of immobilized reactants include surface-immobilized or -localized reagents, e.g., surface-immobilized or -associated enzymes, antibodies, etc. that are interrogated upon the surface, e.g., through fluorescence scanning microscopy or scanning confocal microscopy, total internal reflectance microscopy or fluorometry, microscopy utilizing evanescent waves (see, e.g., U.S. Patent Publication Nos. 20080128627, filed Aug. 31, 2007; 20080152281, filed Oct. 31, 2007; and 200801552280, filed Oct. 31, 2007, all of which are incorporated by reference in their entireties for all purposes), surface imaging, or the like. Various types of solid supports upon which one or more reactants can be immobilized are described above.

In accordance with certain aspects of the invention, a reaction of interest within a first observation region is interrogated for one or more illuminated periods that cumulatively are less than a photo-induced damage threshold period, as set forth elsewhere herein. Such interrogation may occur coincident with or independent of interrogation of additional observation regions on a solid support containing the first observation region. In accordance with the present invention, the observation region typically includes confined reagents (e.g., enzymes, substrates, etc.) that are susceptible to photo-induced damage, and may include an area of a planar or other solid support upon which confined reagents are immobilized. Alternatively or additionally, the observation region may include a physical confinement that constrains the reagents that are susceptible to photo-induced damage, including, e.g., microwells, nanowells, planar surfaces that include hydrophobic barriers to confine reagents.

In accordance with certain aspects of the invention, a reaction of interest within a first observation region is intermittently interrogated under constant illumination by virtue of intermittent presence of detectable components of the reaction, wherein the presence of such detectable components has the potential to directly or indirectly cause photo-induced damage to one or more other reaction components. For example, a buffer comprising detectable components of a reaction can be temporarily replaced with a buffer comprising non-detectable versions of the same components of the reaction, thereby interrupting data acquisition for the reaction. When data acquisition is to be recommenced, the buffer comprising detectable component is substituted for the buffer comprising non-detectable components. This substitution of reaction components may be repeated multiple times to generate multiple sets of data collected at noncontiguous stages of the reaction. For example, such a substitution can occur at least about 2, 4, 6, 8, or 10 times during the course of the reaction.

In certain preferred embodiments, the detectable components are fluorescently-labeled components that can be damaged by exposure to excitation illumination, and can further cause damage to other reaction components, as described above. For example, a sequencing-by-incorporation reaction can be initiated in the presence of fluorescently-labeled nucleotides whose incorporation is indicative of the nucleotide sequence of the nascent strand synthesized by a polymerase, and by complementarity, of the template nucleic acid molecule. At a selected time point during the ongoing reaction, the labeled nucleotides can be removed and replaced with unlabeled nucleotides, for example, by buffer exchange. After a period of time during which data acquisition has been interrupted by the absence of signal from the ongoing reaction, the labeled nucleotides can be reintroduced to reinitiate data acquisition. The labeled nucleotides may be removed and reintroduced multiple times and for various lengths of time, as preferred by the ordinary practitioner. In this way, multiple noncontiguous sequence reads can be generated from a single nucleic acid molecule in real time.

The methods herein slow the accumulation of photo-induced damage to one or more reagents, and may therefore indirectly mitigate the impact of photo-induced damage in an ongoing reaction of interest. By way of example, methods that reduce exposure of a critical enzyme component to illumination radiation (e.g., by subjecting the reaction to periods of non-illumination or by temporarily removing a component of the reaction responsible for such damage) do not necessarily prevent the photo-induced damage to the enzyme component, but rather extend the photo-induced damage threshold period by slowing the accumulation of photo-induced damage in the reaction mixture. Measurements of reduction of photo-induced damage as a result of implementation of intermittent illumination may be characterized as providing a reduction in the level of photo-induced damage as compared to a reaction subjected to constant illumination. Likewise, measurements of reduction of photo-induced damage as a result of temporary removal of reaction components responsible for such damage may be characterized as providing a reduction in the level of photo-induced damage as compared to a reaction in which such components are present throughout. Further, characterization of a reduction in photo-induced damage generally utilizes a comparison of reaction rates, durations, or fidelities, processivities, e.g., of enzyme activity, and/or a comparison of the photo-induced damage threshold period, between a reaction mixture subjected to such the methods and/or systems of the invention and a reaction mixture not so subjected.

In the case of the present invention, implementation of the methods, devices, and systems of the invention generally results in a reduction of photo-induced damage of one or more reactants in a given reaction, as measured in terms of "prevented loss of reactivity" in the system. Using methods known in the art, the amount of prevented loss of activity can at least 10%, preferably greater than 20%, 30%, or 40%, and more preferably at least 50% reduction in loss of reactivity or increase in processivity, and in many cases greater than a 90% and up to and greater than 99% reduction in loss of reactivity or increase in processivity. By way of illustration, and purely for the purpose of example, when referring to reduction in photo-induced damage as a measure of enzyme activity in the presence and absence of intermittent illumination, if a reaction included a reaction mixture having 100 units of enzyme activity that would, under constant illumination, yield a reaction mixture having only 50 units of activity, then a 10% reduction in photo-induced damage would yield a final reaction mixture of 55 units (e.g., 10% of the 50 units otherwise lost, would no longer be lost). Further, use of the invention is expected to increase the performance (e.g., processivity, duration, fidelity, rate, etc.) of a reaction whose performance is negatively impacted by constant exposure to illumination by at least about 2-, 5-, 10-, 20-, 30-, 50-, 80-, 100-, 500-, or 1000-fold over that achieved by the reaction under constant illumination. For example, it is a specific object of the instant invention to increase the processivity of a polymerase enzyme in a sequencing reaction to allow collection of data across a longer length of the template.

With regards to sequencing applications, the methods herein facilitate the scaffolding of nucleic acid sequences in reactions susceptible to photo-induced damage. For example, if the sequencing device has 1000 base pair average readlength under constant illumination, one could subject the reaction to illuminated periods timed to allow approximately 100 nucleotides to be incorporated into the nascent strand of read, followed by non-illuminated periods timed to allow approximately 1000 nucleotides to be incorporated "in the dark." The sequence reads resulting from this experimental design would comprise about ten sequence reads of about 100 nucleotides each separated by gaps of about 1000 nucleotides each. If a plurality of sequencing reactions were carried out in this manner, and the illuminated periods were staggered appropriately, the reads from the plurality of reactions could be combined to provide nucleotide sequence data for the entire template nucleic acid. This would potentially allow sequence scaffolds to be built much more easily than can be done with short-read systems, enabling structural analysis of previously impossible-to-sequence sections of highly repetitive DNA, given the sequencing system is capable of long reads in the absence of photodamage.

IV. SOFTWARE AND ALGORITHM IMPLEMENTATIONS

The methods herein may operate with numerous methods for sequence alignment including those generated by various types of known multiple sequence alignment (MSA) algorithms. For example, the sequence alignment may comprise one or more MSA algorithm-derived alignments that align each read using a reference sequence. In some embodiments in which a reference sequence is known for the region containing the target sequence, the reference sequence can be used to produce an MSA using a variant of the center-star algorithm. Alternatively, the sequence alignment may comprise one or more MSA algorithm-derived alignments that align each read relative to every other read without using a reference sequence ("de novo assembly routines"), e.g., PHRAP, CAP, ClustalW, T-Coffee, AMOS make-consensus, or other dynamic programming MSAs. Depending on the sequence-generating methods used, the determination of sequence alignment may also involve analysis of read quality (e.g., using TraceTuner™, Phred, etc.), signal intensity, peak data (e.g., height, width, proximity to neighboring peak(s), etc.), information indicative of the orientation of the read (e.g., 5'→3' designations), clear range identifiers indicative of the usable range of calls in the sequence, and the like. Additional algorithms and systems for sequence alignment are well know to those of skill in the art, and are described further, e.g., in G. A. Churchill, M. S. Waterman (1992) "The Accuracy of DNA Sequences: Estimating Sequence Quality," *Genomics* 14: 89-98; M. Stephens, et al. (2006) "Automating sequence-based detection and genotyping of SNPs from diploid samples," *Nat. Genet.*, 38: 375-381; J. Hein (1989) *Mol Biol. Evol.*, 6: 649-668; U.S. Ser. No. 12/134,186, filed Jun. 5, 2008; and U.S. Ser. No. 61/116,439, filed Nov. 20, 2008.

A standard sequence alignment problem in the context of DNA sequencing is to align the sequence of a relatively short fragment (<2 kilobases) to a large target sequence. The assumption is made that this fragment represents a contiguous portion of DNA to be mapped to a single location on the reference sequence. With the further development of nucleic acid sequencing technologies (e.g., from Illumina, Inc. (San Diego, Calif.), Helicos BioSciences (Cambridge, Mass.), and Applied Biosystems, Inc. (Foster City, Calif.)) and mate-pair sequencing protocols (see, e.g., U.S. Patent Pub. No. 2006/0292611 A1, which is incorporated by reference herein in its entirety for all purposes), the alignment problem has been extended to align two fragments coming from the same read to the reference sequence using some knowledge of the expected mate-pair configuration (distance and orientation).

With regards to mate-paired reads, mapping two fragments with a distance constraint and orientation constraint has been treated by various short-read mapping algorithms, e.g., R Li, Y Li, K Kristiansen, J Wang. "SOAP: short oligonucleotide alignment program." *Bioinformatics*, 24, 713-714 (2008); and Maq, a set of programs that map and assemble fixed-length Solexa/SOLiD reads (SourceForge, Inc.). While these algorithms can handle simple cases of mate-pair alignment, which generally treat the specific problem of only two reads coming from a mate-paired sequence and use the distance constraint as a hard filter (i.e., if two reads are within x bp of each other and in the correct orientations, report them as a mate-pair hit), the methods provided herein are more general and can handle much more complex data sets, including those with multiple reads, those for which a reference sequence is or is not present, potential non-template sequence (e.g., adapter regions or linker portions described below), and complex distance and orientation constraints.

Real-time single molecule sequencing presents opportunities for obtaining much more complex sequence fragments from a single DNA sequencing read. Two examples are the reading of multiple discontiguous sequence fragments from a single long stretch of DNA using a pulsed or intermittent detection system (e.g., intermittent illumination) as described herein and the contiguous reading of forward, reverse and adapter fragments from a circular templates (SMRTbell™ templates; see e.g., U.S. Ser. No. 61/099,696, filed Sep. 24, 2008; U.S. patent application Ser. No. 12/383,855, filed Mar. 27, 2009 and U.S. patent application Ser. No. 12/413,258, filed Mar. 27, 2009, all of which are incorporated by reference herein in their entireties for all purposes).

Certain aspects of the invention provide methods for optimally aligning such sequences to a reference sequence using knowledge of the molecular configuration and/or sequencing protocol used to generate the related sequence reads. In particular, methods are provided to address the general problem of mapping multiple fragments to a reference sequence with variable distance and orientation constraints.

Beginning with raw sequence data generated by a nucleic acid sequencing instrument (step 1), the sequence data is mapped to a target sequence (step 2) using a local alignment method which produces sub-optimal local alignments as well as the optimal alignment, for example, the Smith-Waterman algorithm. Another, more flexible example of a local alignment method is a chaining method using a method for aligning very short fragments to the target sequence (e.g., kmer-indexing, suffix trees, suffix arrays, etc.) and chaining the resulting hits back into longer chains of significant matches (see, e.g. D. Gusfield, *Algorithms on Strings, Trees, and Sequences*, Cambridge University Press: Cambridge, UK, 1997, which is incorporated by reference herein in its entirety for all purposes). The chains do not necessarily need to be refined by dynamic programming in order to be useful for the following algorithm, permitting a very fast algorithm. In certain embodiments, dynamic-programming refinement of the chain might improve the power (area under the ROC curve) of the algorithm.

Figure 6:
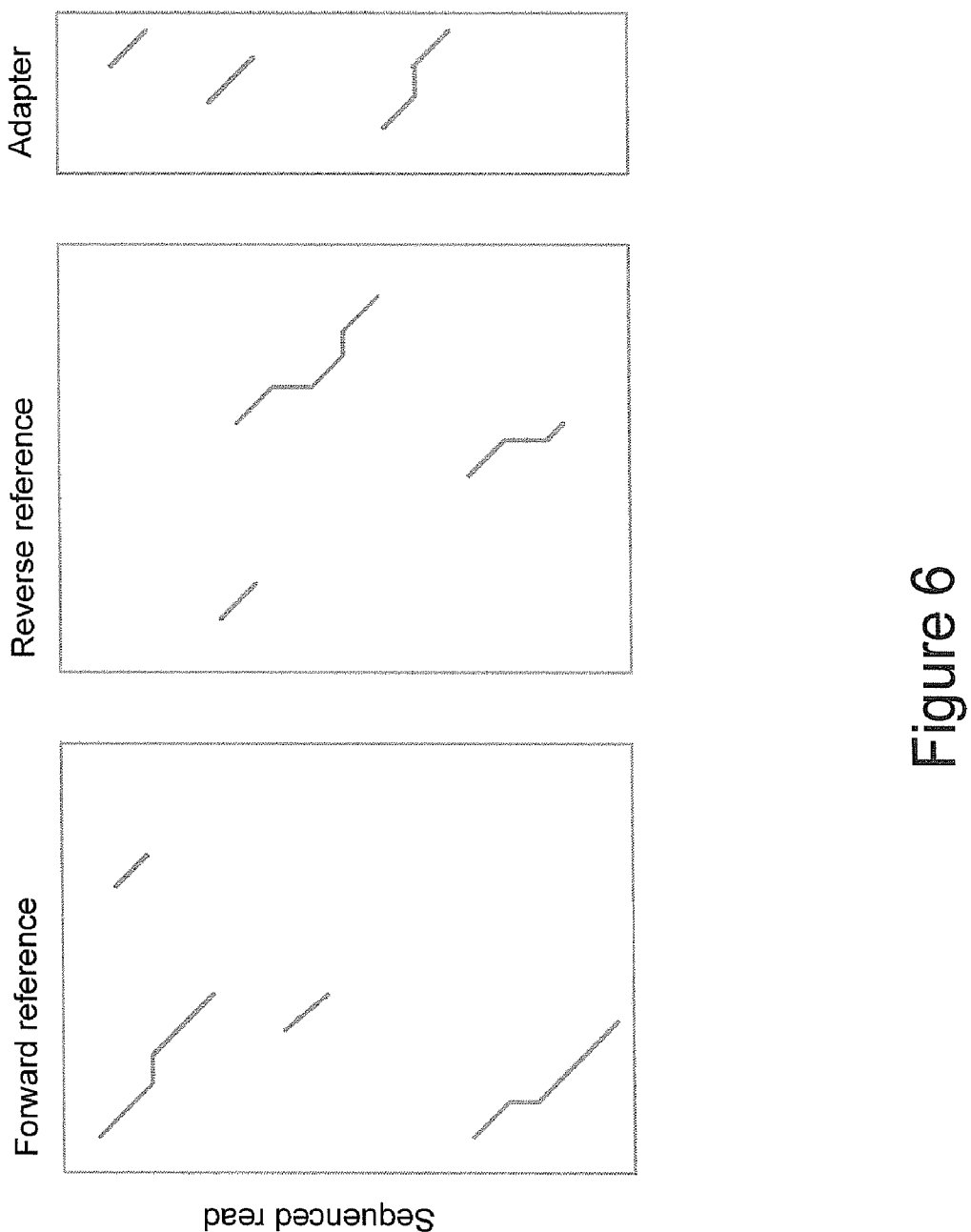
FIG. 6 provides an illustration of paths in a sequence alignment matrix representing sequencing data from a SMRTbell™ template.

The target sequence consists of the potential hypotheses for the molecular template in question. In the example of nucleic acid sequencing methods using iterative illumination for sequencing a shotgun fragment from a linear DNA sequence, the potential hypotheses are both orientations of the genome (since we do not know the original orientation of the fragment). In the example of sequencing of a SMRTbell™ template (e.g., see Example 1 herein), the hypotheses include both orientations of the genome and known adapter sequences. The parameters determining how many hits are reported for each local fragment can be varied to change the specificity and sensitivity of this algorithm. FIG. 6 shows what these hits might look like for a SMRTbell™ template (represented as paths in the sequence alignment matrix, which is often called the dynamic-programming matrix, although it isn't necessary to use dynamic programming to find these paths).

After the potential local alignments have been enumerated, a weighted directed graph is constructed with each local alignment represented as a node in the graph (step 3). The edges are drawn between nodes if they represent a potential reconstruction of the original molecular template using knowledge of the expected molecular configuration. The directed connection of an alignment path A to an alignment path B is interpreted as "The target sequence represented by B could follow the target sequence represented by A in the original molecule." For example, if a linear DNA molecule is being sequenced by a method that uses iterative illumination, then fragments from opposite orientations would not be expected to be connected. In general, fragments that represent the same stretch of the sequencing read but that align to different regions on the target sequence would not be connected. Aside from these examples, the rules for connecting nodes should be fairly loose to permit exploration of weak possibilities that gain significance when all the evidence (e.g. all the sequence reads) are considered. The assignment of edge weights handles the proper weighting of the likelihood of these edges, and the speed of the algorithm can be tuned by optimizing the pruning of highly unlikely edges. As usual this represents a tradeoff between speed and sensitivity.

Weights are assigned to connections (A→B) in the graph representing the log-likelihood that target fragment A is followed by target fragment B in the original molecule.

$$w(A \to B) = -\log P(B|A)$$

The conditional probability $P(B|A)$ encodes the knowledge of the possible molecular configurations and the alignment significance of B.

$$P(B|A) = f(B)g(A,B)$$

where f is a measure of alignment significance (either theoretical or empirically obtained) and g encodes the physical constraints representing the allowed molecular configurations.

For example, in the context of sequencing using iterative illumination the following may be known: the time between the end of one fragment and the beginning of the next fragment is 200 seconds. If the polymerase incorporates bases with an average rate of 4 bp/sec with a standard deviation of 1 bp/sec, it can be hypothesized that the probability of target fragment 2 following target fragment 1 is determined by the distance between these fragments on the target and a normal probability:

$$g(A, B) = \frac{1}{\sqrt{2\pi(200)}} \exp[-(d-800)/2(200)^2]$$

In a SMRTbell™ template example, knowledge of the expected insert size and the observed distance and orientation between fragments would be used to weight the likelihood that these two fragments could come from a correctly generated SMRTbell™ template. This weight could include the expected rate of the polymerase as well and rules for the orientation of fragments with respect to each other and their distance apart in the original read. For example, while it may be expected that two forward fragments mapping to the same region in the target genome potentially come from multiple passes around a SMRTbell™ template molecule, those fragments would not be expected to be immediately adjacent in sequencing time. The weighting function would account for the proper amount of expected time between such fragments (i.e. the elapsed time would be expected to be long enough to include two adapter sequences and a reverse sequence).

In general, the weighting function could be arbitrarily complex and tuned to empirically observed relationships between sequencing fragments given the available knowledge (distance between fragments on the target sequence, sequencing time between fragments, expected length of the template, etc.). For example, the empirical probability distributions might be observed to exhibit longer tails than a Gaussian probability model might predict. The use of a conditional log-likelihood for the assignment of edge weights is motivated by the following logic. In a graph of possible local alignments it is desirable to find a highly likely path that best explains the observed data. Consider a path through three nodes A, B, and C, with P(ABC) being the probability that ABC is the correct assignment:

$$P(ABC) = P(C|AB)P(B|A)P(A) \approx P(C|B)P(B|A)P(A)$$

where the last approximation is justified by the observation that the constraints between allowable assignments to the target sequence are typically local in nature. Generalizing this formula for a path $a_1, \ldots, a_N$ and taking the negative logarithm of both sides gives $$-\log P(a_1 \ldots a_N) = -\sum_{i=1}^{N-1} \log P(a_{i+1}|a_i) - \log P(a_1)$$

Figure 7:
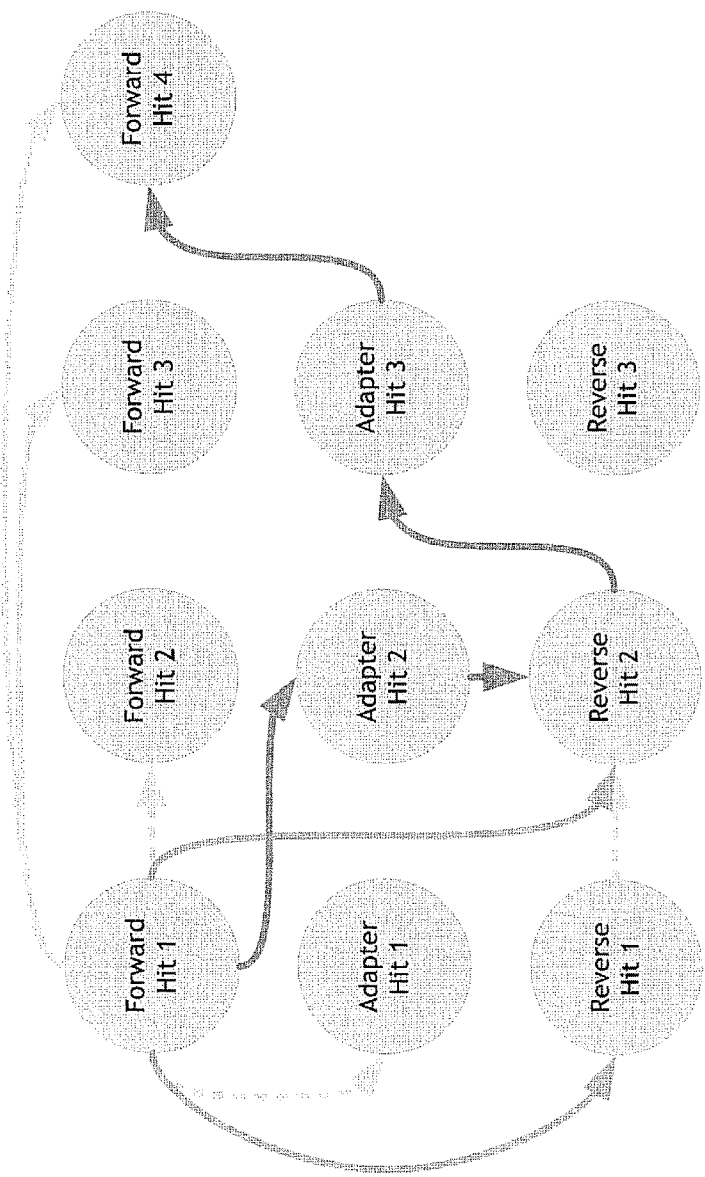
FIG. 7 illustrates a hypothetical directed graph.

It is apparent that the edge weights are additive if we use log-likelihood and we can use standard shortest-path algorithms for directed graphs to find the optimal path. A hypothetical directed graph is illustrated in FIG. 7. This graph corresponds to the situation depicted by the alignments pictured above. Heavier lines correspond to more likely paths with the optimal path shown in blue. Dashed lines represent forbidden transitions. Not all paths are considered in the illustration to avoid clutter in the presentation. The general formula listed above includes a "one-body" term $P(a_1)$ for the starting node in each path that weights the probability that this initial alignment is correct. To accommodate this probability in a path-finding algorithm we add a pseudo-source s to the graph which connects to every possible node (not shown in the graph above). The edge weight connecting the psedosource with a node $a_i$ is $-\log P(a_i)$. This allows the use of a conventional single-source shortest-path algorithm starting from the pseudo-source. The desired probability $P(a_i)$ can come from a measure of alignment significance (theoretical or empirically determined) or could be set uniformly across all alignments to allow the path logic to determine the best path assignment, independent of the relative value of the starting points. It is anticipated that a threshold will be required here to only allow edges between the pseudo-source and nodes for highly likely alignments; otherwise the shortest path algorithm in the next step will not give the desired path.

After construction of the weighted directed graph, the shortest path to each node is determined (step 4). The graph is directed and acyclic (DAG) so we can use the standard shortest-path DAG algorithm (see T. H. Cormen, C E Leiserson, R L Rivest, *Introduction to Algorithms*, MIT Press: Cambridge, Mass., 1990). This algorithm scales as O(V+E) and should be very quick for these graphs. After the shortest path to each node is determined, the paths need to be ranked to declare the best assignment. It is suggested that the best metric would be a measure which rewards paths that explain more of the sequenced read (longer paths) with high likelihood. One such metric would be the normalized negative log-likelihood: dividing the total weight of the path by the number of bases in the sequenced read explained by this path. For more complicated graphs or edge-weight assignments, Dijkstra's algorithm, the Bellman-Ford algorithm, or the A* algorithm could be applied. Other algorithms that may also be used include, but are not limited to the Floyd-Warshall algorithm.

For noisy sequence data it is likely that the local alignments found in step 2 will occasionally overlap with each other in the sequenced read even though it is physically impossible for such overlaps to occur in a perfect system. As such, some amount of slack must be allowed in the edge assignment logic in step 3 to account for not knowing the precise boundaries of each local alignment. Once the best physical model explaining the observed read is determined, the boundaries of the local alignments can be refined to reflect the physical necessity that each base in the sequenced read can only be represented in one local alignment. It is also desirable to explain all of the bases in between the local alignments that haven't been assigned in the graph. One straightforward approach to refinement would be to construct the perfect model of the sequence and to realign the sequenced read to this sequence. This refinement algorithm would preserve physical constraints (each base in the sequenced read can only be explained by one location in the template) and would assign all bases between the extremal nodes in the optimal path.

Certain aspects of the software and algorithm implementations described herein may be varied or altered without departing from the spirit and scope of the invention. For example, with regards to algorithm seeding, many algorithms can be applied for the original determination of sub-optimal local alignments (step 2). Conventional examples include FASTA, BLAST, or Smith-Waterman. It is expected that the best benefit will be obtained from using short-sequence alignment algorithms (suffix array, suffix tree, Boyer-Moore, Rabin-Karp, kmer-indexing, and the like) followed by chaining to establish regions of significant matches. An advantage of the algorithm described here is that it does not require dynamic-programming refinement of the resulting chains and therefore can be quite fast, however it is expected that using dynamic programming to refine the chains in step 2 could increase the power of the algorithm.

With regards to graph construction, there will be advantages to tuning the logic of edge assignments to keep the size of the graph manageable. It is possible that steps 2 and 3 might be combined to in a greedy fashion to focus the potentially slow step 2 into productive areas of the graph. For example, if a particularly strong hit is found early in step 2, then it may be beneficial to search for sub-optimal hits only in this local vicinity, knowing that this strong hit should be in the final solution. Tuning of the graph construction might include thresholds, below which edges are not created. Further, there are multiple parameters (minimum chain length, minimum probability for edge assignment, relative weighting of length vs. accuracy, etc.) which can be exposed and tuned in this algorithm to maximize the sensitivity and specificity of the algorithm for a given scenario.

Although useful in certain preferred embodiments of the invention, the algorithm as presented above does not easily handle the case where the template does not match a physically-motivated expected model. A relevant example of such a case is when the template contains a genomic structural variation (SV), such as translocation, whereby two fragments which are correctly adjacent in the template are located very far apart in the reference genome. Such structural variation cases are best handled in the context of the current algorithm by reporting the confidence of an observed path and reporting situations when no physically expected path seems to fit the observed data. In general, the detection of structural variation requires the presence of multiple highly significant local alignments which can be identified as significantly overturning the null hypothesis of matching the genomic ordering of fragments with their own individual merit. Nevertheless, with molecular redundant sequencing such as SMRTbell™ template sequencing the current algorithm can be adapted to improve the ability to identify an SV event. Such a modification could be a feedback approach which allows modification of the linking constraints in step 3 to allow very far separations on the target sequence when the individual alignments are very significant. Only one such highly-significant pair would be needed to enable the rescue of less significant partial matches that support the same SV hypothesis.

The software and algorithm implementations provided herein are particularly suited for transforming sequence read data generated from various sequencing technologies (e.g., sequencing-by-synthesis, intramolecular redundant sequencing, Sanger sequencing, capillary electrophoretic sequencing, pyrosequencing, ligase-mediated sequencing, etc.) into consensus sequence data that provides a representation of the actual nucleotide sequence of the template nucleic acid that was subjected to the sequencing reaction(s) from which the sequence read data was generated. The software and algorithm implementations provided herein are preferably machine-implemented methods. The various steps recited herein are preferably performed via a user interface implemented in a machine that comprises instructions stored in machine-readable medium and a processor that executes the instructions. The results of these methods are preferably stored on a machine-readable medium, as well. Further, the invention provides a computer program product comprising a computer usable medium having a computer readable program code embodied therein, the computer readable program code adapted to implement one or more of the methods described herein, and optionally also providing storage for the results of the methods of the invention.

In another aspect, the invention provides data processing systems for transforming sequence read data from one or more sequencing reactions into consensus sequence data representative of an actual sequence of one or more template nucleic acids analyzed in the one or more sequencing reactions. Such data processing systems typically comprise a computer processor for processing the sequence read data according to the steps and methods described herein, and computer usable medium for storage of the initial sequence read data and/or the results of one or more steps of the transformation (e.g., the consensus sequence data).

While described with reference to certain specific applications above, it will be understood that these methods are also applicable to other types of complex data sets, and the invention should not be limited to only the specific examples provided herein. Other applications of the instant methods will be clear to those of ordinary skill in the art and are considered to be additional aspects of the instant invention.

V. DEVICES AND SYSTEMS

The invention also provides systems that are used in conjunction with the compositions and methods of the invention in order to provide for intermittent detection of analytical reactions. In particular, such systems typically include the reagent systems described herein, in conjunction with an analytical system, e.g., for detecting data from those reagent systems. For example, a sequencing reaction may be subjected to intermittent illumination, and the sequencing system may include the system components provided with or sold for use with commercially available nucleic acid sequencing systems, such as the Genome Analyzer System available from Illumina, Inc., the GS FLX System, available from 454 Life Sciences, or the ABI 3730 System available from Life Technologies, Inc.

In certain preferred embodiments, reactions subjected to intermittent illumination are monitored using an optical system capable of detecting and/or monitoring interactions between reactants at the single-molecule level. Such an optical system achieves these functions by first generating and transmitting an incident wavelength to the reactants, followed by collecting and analyzing the optical signals from the reactants. Such systems typically employ an optical train that directs signals from the reactions to a detector, and in certain embodiments in which a plurality of reactions is disposed on a solid surface, such systems typically direct signals from the solid surface (e.g., array of confinements) onto different locations of an array-based detector to simultaneously detect multiple different optical signals from each of multiple different reactions. In particular, the optical trains typically include optical gratings or wedge prisms to simultaneously direct and separate signals having differing spectral characteristics from each confinement in an array to different locations on an array based detector, e.g., a CCD, and may also comprise additional optical transmission elements and optical reflection elements.

An optical system applicable for use with the present invention preferably comprises at least an excitation source and a photon detector. The excitation source generates and transmits incident light used to optically excite the reactants in the reaction. Depending on the intended application, the source of the incident light can be a laser, laser diode, a light-emitting diode (LED), a ultra-violet light bulb, and/or a white light source. Further, the excitation light may be evanescent light, e.g., as in total internal reflection microscopy, certain types of waveguides that carry light to a reaction site (see, e.g., U.S. Application Pub. Nos. 20080128627, 20080152281, and 200801552280), or zero mode waveguides, described below. Where desired, more than one source can be employed simultaneously. The use of multiple sources is particularly desirable in applications that employ multiple different reagent compounds having differing excitation spectra, consequently allowing detection of more than one fluorescent signal to track the interactions of more than one or one type of molecules simultaneously. A wide variety of photon detectors or detector arrays are available in the art. Representative detectors include but are not limited to optical reader, high-efficiency photon detection system, photodiode (e.g avalanche photo diodes (APD)), camera, charge couple device (CCD), electron-multiplying charge-coupled device (EMCCD), intensified charge coupled device (ICCD), and confocal microscope equipped with any of the foregoing detectors. For example, in some embodiments an optical train includes a fluorescence microscope capable of resolving fluorescent signals from individual sequencing complexes. Where desired, the subject arrays of optical confinements contain various alignment aides or keys to facilitate a proper spatial placement of the optical confinement and the excitation sources, the photon detectors, or the optical train as described below.

The subject optical system may also include an optical train whose function can be manifold and may comprise one or more optical transmission or reflection elements. Such optical trains preferably encompass a variety of optical devices that channel light from one location to another in either an altered or unaltered state. First, the optical train collects and/or directs the incident wavelength to the reaction site (e.g., optical confinement). Second, it transmits and/or directs the optical signals emitted from the reactants to the photon detector. Third, it may select and/or modify the optical properties of the incident wavelengths or the emitted wavelengths from the reactants. In certain embodiments, the optical train controls an on/off cycle of the illumination source to provide illuminated and non-illuminated periods to one or more illuminated reaction sites. Illustrative examples of such optical transmission or reflection elements are diffraction gratings, arrayed waveguide gratings (AWG), optic fibers, optical switches, mirrors (including dichroic mirrors), lenses (including microlenses, nanolenses, objective lenses, imaging lenses, and the like), collimators, optical attenuators, filters (e.g., polarization or dichroic filters), prisms, wavelength filters (low-pass, band-pass, or high-pass), planar waveguides, wave-plates, delay lines, and any other devices that guide the transmission of light through proper refractive indices and geometries. One example of a particularly preferred optical train is described in U.S. Patent Pub. No. 20070036511, filed Aug. 11, 2005, and incorporated by reference herein in its entirety for all purposes.

In a preferred embodiment, a reaction site (e.g., optical confinement) containing a reaction of interest is operatively coupled to a photon detector. The reaction site and the respective detector can be spatially aligned (e.g., 1:1 mapping) to permit an efficient collection of optical signals from the reactants. In certain preferred embodiments, a reaction substrate is disposed upon a translation stage, which is typically coupled to appropriate robotics to provide lateral translation of the substrate in two dimensions over a fixed optical train. Alternative embodiments could couple the translation system to the optical train to move that aspect of the system relative to the substrate. For example, a translation stage provide a means of removing a reaction substrate (or a portion thereof) out of the path of illumination to create a non-illuminated period for the reaction substrate (or a portion thereof), and returning the substrate at a later time to initiate a subsequent illuminated period. An exemplary embodiment is provided in U.S. Patent Pub. No. 20070161017, filed Dec. 1, 2006.

In particularly preferred aspects, such systems include arrays of reaction regions, e.g, zero mode waveguide arrays, that are illuminated by the system, in order to detect signals (e.g., fluorescent signals) therefrom, that are in conjunction with analytical reactions being carried out within each reaction region. Each individual reaction region can be operatively coupled to a respective microlens or a nanolens, preferably spatially aligned to optimize the signal collection efficiency. Alternatively, a combination of an objective lens, a spectral filter set or prism for resolving signals of different wavelengths, and an imaging lens can be used in an optical train, to direct optical signals from each confinement to an array detector, e.g., a CCD, and concurrently separate signals from each different confinement into multiple constituent signal elements, e.g., different wavelength spectra, that correspond to different reaction events occurring within each confinement. In preferred embodiments, the setup further comprises means to control illumination of each confinement, and such means may be a feature of the optical system or may be found elsewhere is the system, e.g., as a mask positioned over an array of confinements. Detailed descriptions of such optical systems are provided, e.g, in U.S. Patent Pub. No. 20060063264, filed Sep. 16, 2005, which is incorporated herein by reference in its entirety for all purposes.

The systems of the invention also typically include information processors or computers operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provide for the electronic transfer of data from the detection system to the processor for subsequent analysis and conversion. Operable connections may be accomplished through any of a variety of well known computer networking or connecting methods, e.g., Firewire®, USB connections, wireless connections, WAN or LAN connections, or other connections that preferably include high data transfer rates. The computers also typically include software that analyzes the raw signal data, identifies signal pulses that are likely associated with incorporation events, and identifies bases incorporated during the sequencing reaction, in order to convert or transform the raw signal data into user interpretable sequence data (See, e.g., Published U.S. Patent Application No. 2009-0024331, the full disclosure of which is incorporated herein by reference in its entirety for all purposes).

Exemplary systems are described in detail in, e.g., U.S. patent application Ser. No. 11/901,273, filed Sep. 14, 2007 and U.S. patent application Ser. No. 12/134,186, filed Jun. 5, 2008, the full disclosures of which are incorporated herein by reference in their entirety for all purposes.

Further, as noted above, the invention provides data processing systems for transforming sequence read data into consensus sequence data. In certain embodiments, the data processing systems include machines for generating sequence read data by interrogating a template nucleic acid molecule. In certain preferred embodiments, the machine generates the sequence read data using a sequencing-by-synthesis technology, as described elsewhere herein, but the machine may generate the sequence read data using other sequencing technologies known to those of ordinary skill in the art, e.g., pyrosequencing, ligation-mediated sequencing, Sanger sequencing, capillary electrophoretic sequencing, etc. Such machines and methods for using them are available to the ordinary practioner.

The sequence read data generated is representative of the nucleotide sequence of the template nucleic acid molecule only to the extent that a given sequencing technology is able to generate such data, and so may not be identical to the actual sequence of the template nucleic acid molecule. For example, it may contain a deletion or a different base at a given position as compared to the actual sequence of the template, e.g., when a base call is missed or incorrect, respectively. As such, it is beneficial to generate redundant sequence read data, and the methods described herein provide manipulations and computations that transform redundant sequence read data into consensus sequence data that is generally more representative of the actual sequence of the template nucleic acid molecule than sequence read data from a single read of a single template nucleic acid molecule. Redundant sequence read data comprises multiple reads, each of which includes at least a portion of sequence read that overlaps with at least a portion of at least one other of the multiple reads. As such, the multiple reads need not all overlap with one another, and a first subset may overlap for a different portion of the template nucleic acid sequence than does a second subset. Such redundant sequence read data can be generated by various methods, including repeated sequencing of a single nucleic acid template, sequencing of multiple identical nucleic acid templates, or a combination thereof.

In another aspect, the data processing systems can include software and algorithm implementations provided herein, e.g. those configured to transform redundant sequence read data into consensus sequence data, which, as noted above, is generally more representative of the actual sequence of the template nucleic acid molecule than sequence read data from a single read of a single template nucleic acid molecule.

Further, the transformation of the redundant sequence read data into consensus sequence data identifies and negates some or all of the single-read variation between the multiple reads in the redundant sequence read data. As such, the transformation provides a representation of the actual nucleotide sequence of the nucleic acid template from which redundant sequence read data is generated that is more accurate than a representation based on a single read.

The software and algorithm implementations provided herein are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing redundant sequence read data; c) memory storing software-implemented instructions for carrying out the algorithms for transforming redundant sequence read data into consensus sequence data; d) a processor for executing the instructions; e) software for recording the results of the transformation into memory; and f) memory for recordation and storage of the resulting consensus sequence read data. In preferred embodiments, the user interface is used by the practitioner to manage various aspects of the machine, e.g., to direct the machine to carry out the various steps in the transformation of redundant sequence read data into consensus sequence data, recordation of the results of the transformation, and management of the consensus sequence data stored in memory.

As such, in preferred embodiments, the methods further comprise a transformation of the computer-readable medium by recordation of the redundant sequence read data and/or the consensus sequence data generated by the methods. Further, the computer-readable medium may comprise software for providing a graphical representation of the redundant sequence read data and/or the consensus sequence read data, and the graphical representation may be provided, e.g., in soft-copy (e.g., on an electronic display) and/or hard-copy (e.g., on a print-out) form.

The invention also provides a computer program product comprising a computer-readable medium having a computer-readable program code embodied therein, the computer readable program code adapted to implement one or more of the methods described herein, and optionally also providing storage for the results of the methods of the invention. In certain preferred embodiments, the computer program product comprises the computer-readable medium described above.

In another aspect, the invention provides data processing systems for transforming sequence read data from one or more sequencing reactions into consensus sequence data representative of an actual sequence of one or more template nucleic acids analyzed in the one or more sequencing reactions. Such data processing systems typically comprise a computer processor for processing the sequence read data according to the steps and methods described herein, and computer usable medium for storage of the initial sequence read data and/or the results of one or more steps of the transformation (e.g., the consensus sequence data), such as the computer-readable medium described above.

Figure 9:
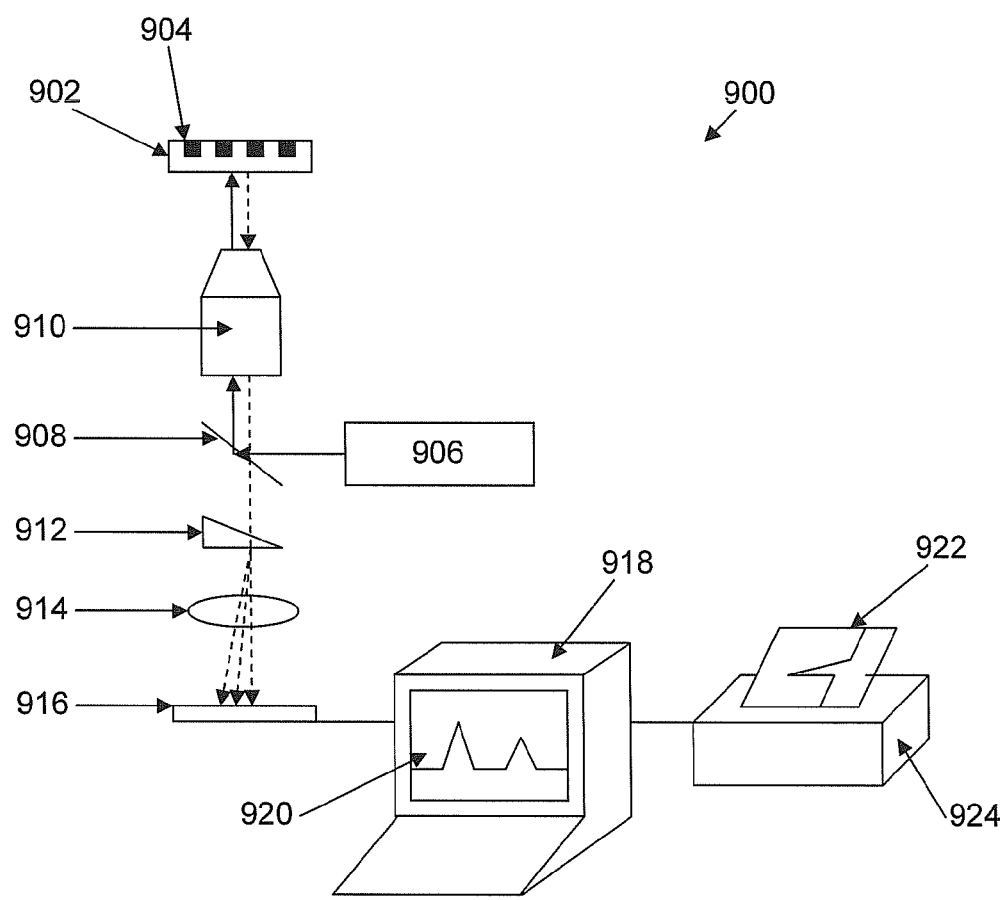
FIG. 9 schematically illustrates one embodiment of a system for use with the methods, devices, and systems of the invention.

As shown in FIG. 9, the system 900 includes a substrate 902 that includes a plurality of discrete sources of chromophore emission signals, e.g., an array of zero mode waveguides 904. An excitation illumination source, e.g., laser 906, is provided in the system and is positioned to direct excitation radiation at the various signal sources. This is typically done by directing excitation radiation at or through appropriate optical components, e.g., dichroic 108 and objective lens 910, that direct the excitation radiation at the substrate 902, and particularly the signal sources 904. Emitted signals from the sources 904 are then collected by the optical components, e.g., objective 910, and passed through additional optical elements, e.g., dichroic 908, prism 912 and lens 914, until they are directed to and impinge upon an optical detection system, e.g., detector array 916. The signals are then detected by detector array 916, and the data from that detection is transmitted to an appropriate data processing system, e.g., computer 918, where the data is subjected to interpretation, analysis, and ultimately presented in a user ready format, e.g., on display 920, or printout 922, from printer 924. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901, 273, all of which are incorporated herein by reference in their entireties for all purposes.)

VI. EXEMPLARY APPLICATIONS

The methods and compositions of the invention are useful in a broad range of analytical reactions in which one or more aspects of a detection method are detrimental to one or more aspects of the analytical reaction, such as rate, duration, fidelity, processivity, and the like. In such cases, intermittent detection at least partially mitigates the detrimental effect while allowing collection of data from stages of the analytical reaction that were previously uncollectable. As noted above, illuminated reactions are one example of analytical reactions that benefit from the compositions and methods described herein, particularly those using photoluminescent or fluorescent reagents, and particularly such reactions where one or more of the reaction components that are susceptible to photo-induced damage are present at relatively low levels. One exemplary application of the methods and compositions described herein is in single molecule analytical reactions, where the reaction of a single molecule (or very limited number of molecules) is observed in the analysis, such as observation of the action of a single enzyme molecule. In another aspect, the present invention is directed to illuminated reactions for single molecule analysis, including sequencing of nucleic acids by observing incorporation of nucleotides into a nascent nucleic acid sequence during template-directed polymerase-based synthesis. Such methods, generally referred to as "sequencing-by-incorporation" or "sequencing-by-synthesis," involve the observation of the addition of nucleotides or nucleotide analogs in a template-dependent fashion in order to determine the sequence of the template strand. See, e.g., U.S. Pat. Nos. 6,780,591, 7,037,687, 7,344, 865, 7,302,146. Processes for performing this detection include the use of fluorescently labeled nucleotide analogs within a confined observation region, e.g., within a nanoscale well and/or tethered, either directly or indirectly to a surface. By using excitation illumination (i.e., illumination of an appropriate wavelength to excite the fluorescent label and induce a detectable signal), the fluorescently labeled bases can be detected as they are incorporated into the nascent strand, thus identifying the nature of the incorporated base, and as a result, the complementary base in the template strand.

In particular aspects, when an analysis relies upon a small population of reagent molecules, damage to any significant fraction of that population will have a substantial impact on the analysis being performed. For example, prolonged interrogation of a limited population of reagents, e.g., fluorescent analogs and enzymes, can lead to photo-induced damage of the various reagents to the point of substantially impacting the activity or functionality of the enzyme. It has been shown that prolonged illumination of DNA polymerases involved in synthesis using fluorescent nucleotide analogs results in a dramatic decrease in the enzyme's ability to synthesize DNA, often measured as a reduction in processivity. Without being bound to any theory of operation, it is believed that in some cases a photo-induced damage event affects the catalytic region of the enzyme thus affecting either the ability of the enzyme to remain complexed with the template, or its ability to continue synthesis. In general, the methods, devices, and systems of the present invention can increase performance and/or selectively monitor one or more stages of an illuminated reaction by subjecting the reaction to intermittent illumination.

One particularly preferred aspect of the invention is in conjunction with the sequencing by incorporation of nucleic acids within an optical confinement, such as a zero-mode waveguide. Such reactions involve observation of an extremely small reaction volume in which one or only a few polymerase enzymes and their fluorescent substrates may be present. Zero-mode waveguides, and their use in sequencing applications are generally described in U.S. Pat. Nos. 6,917, 726 and 7,033,764, and preferred methods of sequencing by incorporation are generally described in Published U.S. Patent Application No. 2003-0044781, the full disclosures of which are incorporated herein by reference in their entireties for all purposes, and in particular for their teachings regarding such sequencing applications and methods. Briefly, arrays of zero-mode waveguides ("ZMWs"), configured in accordance with the present invention may be employed as optical confinements for single molecule DNA sequence determination. In particular, as noted above, these ZMWs provide extremely small observation volumes at or near the transparent substrate surface, also termed the "base" of the ZMW. A nucleic acid synthesis complex, e.g., template sequence, polymerase, and primer, which is immobilized at the base of the ZMW, may then be specifically observed during synthesis to monitor incorporation of nucleotides in a template dependent fashion, and thus provide the identity and sequences of nucleotides in the template strand. This identification is typically accomplished by providing detectable label groups, such as fluorescent labeling molecules, on the nucleotides. In some instances, the labeled nucleotides terminate primer extension, allowing a "one base at a time" interrogation of the complex. If, upon exposure to a given labeled base, a base is incorporated, its representative fluorescent signal may be detected at the base of the ZMW. If no signal is detected, then the base was not incorporated and the complex is interrogated with each of the other bases, in turn. Once a base is incorporated, the labeling group is removed, e.g., through the use of a photocleavable linking group, and where the label was not the terminating group, a terminator, upon the 3' end of the incorporated nucleotide, may be removed prior to subsequent interrogation. In other more preferred embodiments, the incorporation of a labeled nucleotide does not terminate primer extension and the processive incorporation of multiple labeled nucleotides can be monitored in real time by detecting a series of fluorescent signals at the base of the ZMW. In some such embodiments, the label is naturally released upon incorporation of the labeled nucleotides by the polymerase, and so need not be released by alternative means, e.g., a photocleavage event. As such, a processive sequencing reaction can comprise a polymerase enzyme repetitively incorporating multiple nucleotides or nucleotide analogs, as long as such are available to the polymerase within the reaction mixture, e.g., without stalling on the template nucleic acid. (Such a processive polymerization reaction can be prevented by incorporation of nucleotides or nucleotide analogs that contain groups that block additional incorporation events, e.g., certain labeling groups or other chemical modifications.)

In accordance with the present invention, sequencing reactions may be carried out by only interrogating a reaction mixture, e.g., detecting fluorescent emission for one or more illuminated periods before excessive photo-induced damage has occurred. In general, the methods described herein are implemented in a manner sufficient to provide beneficial impact, e.g., reduced photo-induced damage and/or extension of the photo-induced damage threshold period, but are not implemented in such a manner to interfere with the reaction of interest, e.g., a sequencing reaction. The present invention also contemplates alternative methods of and compositions for mitigating the impact of photo-induced damage on a reaction, as described above and in, e.g., U.S. Ser. No. 61/116, 048, filed Nov. 19, 2008. Such alternative methods and compounds can be used in combination with the compositions and methods provided herein to further alleviate the effects of species that can be generated during an illuminated reaction.

Another method of mitigating the impact of photo-induced damage on the results of a given reaction provides for the elimination of potentially damaging oxygen species using means other than the use of the photo-induced damage mitigating agents described above. In one example, dissolved oxygen species may be flushed out of aqueous systems by providing the reaction system under different gas environments, such as by exposing an aqueous reaction to neutral gas environments, such as argon, nitrogen, helium, xenon, or the like, to prevent dissolution of excess oxygen in the reaction mixture. By reducing the initial oxygen load of the system, it has been observed that photo-induced damage effects, e.g., on polymerase mediated DNA synthesis, is markedly reduced. In particularly preferred aspects, the system is exposed to a xenon atmosphere. In particular, since xenon can be induced to form a dipole, it operates as a triplet-state quencher in addition to supplanting oxygen in the aqueous system. (See, e.g., Vierstra and Poff, Plant Physiol. May 1981; 67(5): 996-998) As such, xenon would also be categorized as a quencher, as set forth above.

Although described in terms of zero-mode waveguides, it will be appreciated that a variety of selective illumination strategies may be employed to selectively interrogate different regions of a solid support over time, e.g., so as to only damage molecules within certain selected regions of a substrate while not damaging molecules in other selected regions of the substrate. In certain embodiments, such methods can involve using a directed light source (e.g., a laser) to illuminate only selected regions; changing the illumination angle of the light source; or refocusing the illumination, e.g., by passing the illumination through an optical train that alters the shape of the incident light on the solid support. These and further examples of alternative methods of mitigating photo-induced damage which can be used in combination with methods and systems of the invention described herein are provided in U.S. Patent Pub. No. 20070036511, filed Aug. 11, 2005; U.S. Pat. No. 6,881,312; U.S. Ser. No. 61/116,048, filed Nov. 19, 2008; and U.S. Patent Pub. No. 20070161017, filed Dec. 1, 2006, all of which are incorporated herein by reference in their entireties for all purposes, and in particular for disclosure related to these methods of mitigating photo-induced damage.

As noted above, using templates that allow repeated sequencing (e.g., circular templates, SMRTbell™ templates, etc.) in a single reaction can increase the percent of a nucleic acid template for which nucleotide sequence data is generated and/or increase the fold-coverage of the sequence reads for one or more regions of interest in the template, thereby providing more complete data for further analysis, e.g., construction of sequence scaffolds and/or consensus sequences for the nucleic acid template. For example, in certain preferred embodiments, templates sequenced by the methods described herein are templates comprising a double-stranded segment, e.g., greater than 75%, or even greater than 90% of the target segment will be double-stranded or otherwise internally complementary. Such templates may, for example, comprise a double-stranded portion comprised of two complementary sequences and two single-stranded linking portions (e.g., oligos or "hairpins") joining the 3' end of each strand of the double-stranded region to the 5' end of the other strand (sometimes referred to as "SMRTbell" templates). These template molecules are particularly useful as nucleotide sequence data generated therefrom comprises both sense and antisense nucleotide sequences for the double-stranded portion, and the circular conformation of the template enables repeated sequencing (e.g., using a polymerase capable of strand-displacement) provides duplicative or redundant sequence information. Restated, a sequence process may progress around the completely contiguous sequence repeatedly obtaining sequence data for each segment from the complementary sequences, as well as sequence data within each segment, by repeatedly sequencing that segment. Iterative illumination is useful in such sequencing applications, e.g., to focus nucleotide sequence data collection on stages of the sequencing reaction most of interest, such as the stages during which nucleotide sequence data is being generated from a strand of the (previously) double-stranded portion. Iterative illumination may also allow additional "rounds" of sequencing the template by virtue of the reduction in photo-induced damage to reaction components, as described elsewhere herein, thereby providing more complete and robust nucleotide sequence data for future analysis, e.g., sequence scaffold construction and/or consensus sequence determination.

In addition to providing sense and antisense sequence data within a single template molecule that can be sequenced in one integrated process, the presence of the single-stranded linking portions also provides an opportunity to provide a registration sequence that permits the identification of when one segment, e.g., the sense strand, is completed and the other begins, e.g., the antisense strand. Such registration sequences provide a basis for alignment sequence data from multiple sequence reads from the same template sequences, e.g., the same molecule, or identical molecules in a template population.

In certain embodiments, such a sequencing process begins by priming the template nucleic acid within one of the linking portions and allowing the polymerase to proceed along the strand of the double-stranded portion of the template that is immediately downstream of the primed linking portion when the double-stranded portion is melted or denatured. The sequence process proceeds around the second linking portion and proceeds along the complementary strand of the (now previously) double-stranded portion of the template. Because the template is circular, this process can continue to provide multiple repeated sequence reads from the one template. Thus, sequence redundancy comes from both the determination of complementary sequences (sense and antisense strands of the double-stranded portion), and the repeated sequencing of each circular template. The ongoing sequencing reaction is subjected to multiple illuminated and non-illuminated periods to generate at least two or more sequence reads per pass around the template. The illuminated periods are preferably timed to allow generation of nucleotide sequence data for selected regions of the template. For example, it may be beneficial to only generate nucleotide sequence data for the complementary strands of the double-stranded portion, or segments thereof. As will be appreciated, in iteratively sequencing circular templates, strand displacing polymerases, as discussed elsewhere herein, are particularly preferred, as they will displace the nascent strand with each cycle around the template, allowing continuous sequencing. Other approaches will similarly allow such iterative sequencing including, e.g., use of an enzyme having 5'-3' exonuclease activity in the reaction mixture to digest the nascent strand post-synthesis.

One may optionally employ various means for controlling initiation and/or progression of a sequencing reaction, and such means may include the addition of specific sequences or other moieties into the template nucleic acid, such as binding sites, e.g., for primers or proteins. Various methods of incorporating control elements into an analytical reaction, e.g. by integrating stop or pause points into a template, are discussed elsewhere herein and are further described in related application, U.S. application Ser. No. 12/413,258, filed Mar. 28, 2009, which is incorporated herein by reference in its entirety for all purposes.

In certain embodiments, a reaction stop or pause point may be included within the template sequence, such as a reversibly bound blocking group at one location on the template, e.g., on the linking portion that was not used in priming. By way of example, following initial sequencing from the original priming location, e.g., from the single-stranded linking portion used in priming synthesis through a first portion of the sense strand (e.g., the 3' end), the data acquisition may be switched off and the polymerase allowed to proceed around the template, e.g., through the remainder of the sense strand to the other linking portion. The incorporation of a synthesis blocking group coupled to this linking portion will allow control of reinitiation of the polymerase activity at the 3' end of the antisense strand. One would thereby obtain paired-end sequence data for the overall (previously) double-stranded segment, with sequence data from one end coming from the sense strand and sequence data from the other end coming from the antisense strand. This template construction and sequencing methodology is particularly useful in the case of long double-stranded segments, especially given the short read lengths generated by some sequencing technologies.

A variety of synthesis controlling groups may be employed, including, e.g., large photolabile groups coupled to the nucleobase portion of one or more bases in the single-stranded portion that inhibit polymerase-mediated replication; strand-binding moieties that prevent processive synthesis; non-native nucleotides included within the primer and/or template; and the like. The use of strand-binding moieties includes, but is not limited to, reversible, specific binding of particular proteins to recognition sequences incorporated into the template (or primer bound thereto) for this purpose. In certain embodiments, such control sequences may include binding sites for transcription factors, e.g., repressor binding regions provided within the linking portion(s). For example, the lac repressor recognition sequence is bound by the lac repressor protein, and this binding has been shown to block replication in a manner reversible by addition of appropriate initiators, such as isophenylthiogalactoside (IPTG) or allolactose.

In some embodiments, primer recognition sequences and/or additional control sequences may also be provided for control of initiation and/or progression of polymerization, e.g., through a hybridized probe or reversibly modified nucleotide, or the like. (See, e.g., U.S. Patent Application No. 2008-0009007, the full disclosure of which is incorporated herein by reference in its entirety for all purposes.) Such probes include but are not limited to probes at which a polymerase initiates polymerization, probes containing various types of detectable labels, molecular beacons, TaqMan® probes, Invader® probes (Third Wave Technologies, Inc.), or the like, that can be used for various purposes, e.g., to provide indications of the commencement and/or progress of synthesis.

An engineered pause point can include one or more non-native (non-natural) bases (also termed $5^{th}$ bases) that do not pair with any of the four native nucleoside polyphosphates in the synthesis reaction, e.g., in the template and/or oligonucleotides probe(s). Upon encountering such a base, the polymerase pauses until the complement to the non-natureal base is added to the reaction mixture. Likewise, an engineered pause point could include a "damaged" base that causes a stop in replication until repair enzymes are added to the mixture. For example, a template having a pyrimidine dimer would cause the replication complex to pause, and addition of the photolyase DNA repair enzyme would repair the problem location and allow replication, and sequencing to continue.

In some cases, it may be desirable to provide endonuclease recognition sites within the template nucleic acid. For example, inclusion of such sites within a circular template can allow for a mechanism to release the template from a synthesis reaction, i.e., by linearizing it, and allowing the polymerase to run off the linear template, and/or to expose the template to exonuclease activity, and thus terminate synthesis through removal of the template. Such sites could additionally be exploited as control sequences by providing specific binding locations for endonucleases engineered to lack cleavage activity, but retain sequence specific binding, and could therefore be used to block progression of the polymerase enzyme on a template nucleic acid.

In some cases, nicking sites, e.g., sites recognized by nicking endonucleases, may be included within a portion of the template molecule, and particularly within a double-stranded portion of the template, e.g., in a double-stranded segment of a SMRT bell™ or in the stem portion of an exogenous hairpin structure. Such nicking sites provide one or more breaks in one strand of a double-stranded sequence and can thereby provide one or more priming locations for, e.g., a strand-displacing polymerase enzyme. A variety of nicking enzymes and their recognition sequences are known in the art, with such enzymes being generally commercially available, e.g., from New England Biolabs.

In certain embodiments, methods for intermittent detection described herein are useful in "paired-end" sequencing applications in which sequence information is generated from two ends of a template nucleic acid but not for at least a portion of the intervening portion of the template. Typically, paired-end sequencing applications provide sequence data for only the two ends of a nucleic acid template, but the present invention also allows generation of additional sequence reads that are noncontiguous with the sequence reads from the ends of the template. In certain preferred embodiments, a duplex fragment (e.g., genomic fragment) is ligated to a single-stranded linker that connects the 3' end of the sense strand to the 5' end of the antisense strand, or that connects the 5' end of the sense strand to the 3' end of the antisense strand. In either orientation, separation of the two strands of the duplex fragment results in a single-stranded linear template nucleic acid that contains the linker in between the sense and antisense strands. Subsequent sequencing can involve intermittent detection that generates sequence reads for only the portions of the sense and antisense strands that are of interest, e.g., one or both of the ends. In certain embodiments, both sense and antisense strands may be sequenced at both ends to provide redundancy in the sequence data. Sequence reads recognized as being from the linker portion of the template (e.g., based on the known linker sequence or specific registration sequences encoded therein) can be used to orient the alignment of the sequence reads from the sense and antisense portions of the template, providing context for determining the sequences of the ends of the duplex fragment and subsequent sequence scaffold construction and/or mapping. In certain embodiments, pause or stop points may be incorporated into the linker to control the processing of the template by the polymerase, and therefore may be used to synchronize the detection periods to ensure generation of sequence reads from particular regions of template. Further, additional detection periods can be included that are timed to provide sequence reads from portions of the sense and/or antisense strand that are noncontiguous with the end regions.

In a related embodiment, paired-end sequencing may be accomplished by using a nucleic acid template that has linkers connecting the sense and antisense strands of a duplex fragment at both ends, such that separation of the strands of the duplex fragment provides a single-stranded circular template that contains a linkers in between each end of the sense and antisense strands of the original duplex fragment. Such a template molecule would allow a strand-displacing polymerase to proceed around the template multiple times, thereby potentially generating redundant sequence data from both ends of both strands of the original duplex fragment. As noted elsewhere herein, such redundancy is useful for determination of consensus sequences and/or construction of sequence scaffolds. As the polymerase enzyme processes the template, detection periods can be timed (e.g., based on knowledge of the rate at which the polymerase processes the template) to generate nucleotide sequence reads from the regions of the template corresponding to one or both ends of the sense and antisense strands, and can also include detection periods to generate additional reads from other, noncontiguous regions of the duplex fragment, as well. Although such timing can be used to determine the appropriate periodicity of the detection periods, at later stages of the reaction (e.g., as the polymerase repeatedly proceeds around the template), the exact location of reinitiation of sequence read generation becomes more approximate. Incorporation of pause or stop points into one or both linkers to regulate the processing of the template by the polymerase may be used to synchronize the detection periods regardless of the total distance travelled by the polymerase around the template. This strategy more reliably ensures generation of sequence reads from selected regions of template, e.g, the ends of the sense and antisense portions and, optionally, regions in between and noncontiguous with the end regions regardless of the number of passes of the polymerase around the template nucleic acid, especially in later stages of the reaction. Further, the known sequence of one or both of the linkers can be used to orient sequence reads from the sense and antisense portions for consensus sequence determination and/or mapping.

Interestingly, the use of the sense/antisense nucleic acid templates described above would represent a unidirectional processing of a template to provide paired-end sequence data, as opposed to the more traditional bi-directional processing of a linear template molecule. Further, unlike traditional approaches, these methods for paired-end sequencing involve processing, chemically or otherwise, of not just the regions at the ends, but also regions in between the ends, and in some embodiments comprising processing of the entire template. For example, a polymerase incorporates nucleotides into a nascent strand for each position of the template (thereby "processing" each position of the template), yet the sequencing data generated is limited to specific regions of the template that are of particular interest to the practitioner, such as the end regions.

In certain embodiments, methods for intermittent detection described herein are useful in analysis systems that employ nanopores. A nanopore is a small pore in an electrically insulating membrane that can be used for single molecule detection. In general, a nanopore functions as a Coulter counter for much smaller particles, and can take various forms, e.g., a protein channel in a lipid bilayer or a pore in a solid-state membrane. The detection principal is based on monitoring the ionic current of an electrolyte solution passing through the nanopore as a voltage is applied across the membrane. For example, passage of a polynucleotide molecule (e.g., DNA, RNA, etc.) through a nanopore causes changes in the magnitude of the current through the nanopore, with each nucleotide obstructing the nanopore to a different, characteristic degree. As such, the pattern of variations in the current passing through the nanopore as the polynucleotide is drawn through may be monitored and analyzed to determine the nucleotide sequence of the polynucleotide. A polynucleotide may be drawn through the nanopore by various means, e.g., by electrophoresis, or using enzyme chaperones to guide the polynucleotide through the nanopore. For additional discussion of methods of fabrication and use of nanopores, see, e.g., U.S. Pat. No. 5,795,782; Kasianowicz, J. J., et al. (1996) *Proc Natl Acad Sci USA* 93(24):13770-3; Ashkenas, N., et al. (2005) *Angew Chem Int Ed Engl* 44(9):1401-4; Winters-Hilt, S., et al. (2003) *Biophys J* 84:967-76; Astier, Y., et al. (2006) *J Am Chem Soc* 128(5):1705-10; Fologea, D., et al. (2005) *Nano Lett* 5(10):1905-9; Deamer, D. W., et al. (2000) *Trends Biotechnol* 18(4):147-51; and Church, G. M. (2006) *Scientific American* 294(1):52, all of which are incorporated by reference herein in their entireties for all purposes. In some embodiments, intermittent detection of nucleic acid sequence data from a nanopore may be achieved by modifying the progress of the polynucleotide through the nanopore so that progress is sped up during non-detection periods and progress is slowed to allow sequence determination during detection periods. The rate of passage of the polynucleotide through the nanopore may be modified by various methods, including but not limited to increasing an electrophoretic field carrying the polynucleotide (e.g., by increasing the voltage, changing the conductivity of the reaction mixture, and the like), or changing various reaction conditions to alter the speed at which a protein chaperone carries the polynucleotide. Further, in embodiments utilizing a processive exonuclease to feed individual bases through the nanopore, the kinetics of the exonuclease may be modified based on the known biochemical characteristics of the exonuclease.

In diagnostic sequencing applications, it may be necessary only to provide sequence data for a small fragment of DNA, but do so in an extremely accurate sequencing process. For such applications, shorter target segments may be employed, thus permitting a higher level of redundancy by sequencing multiple times around a smaller circular template, where such redundancy provides the desired accuracy. Thus, in some cases, the double stranded target segment may be much shorter, e.g., from 10 to 200, from 20 to 100 or from 20 to 50 or from 20 to 75 bases in length. For purposes of the foregoing, the length of the target segment in terms of bases denotes the length of one strand of the double stranded segment. In such applications, various methods for intermittent detection described herein may be used to analyze the sequence of the template, thereby targeting the sequence data to the portion(s) of the template of particular interest to the diagnostician, and/or improving various aspects of the reaction performance, e.g., by virtue of the reduction of photo-induced damage to one or more reaction components.

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

The following non-limiting examples are provided to further illustrate the invention.

VI. EXAMPLE 1

Intermittent Illumination of a Single Molecule Sequencing-By-Synthesis Reaction A nucleic acid template was provided that comprised a double-stranded region and two single-stranded linker portions at each end. The first linker portion connected the 3' end of the sense strand with the 5' end of the antisense strand, and the second linker portion connected the 3' end of the antisense strand with the 5' end of the sense strand. This template was designed to form a single-stranded circle of approximately 500 bases when the double-stranded region was opened (e.g., by heat denaturization, helicase activity, etc.), and is sometimes referred to as a SMRTbell™ template. A plurality of this nucleic acid template was incubated with polymerases, primers, and other reaction components to allow formation of polymerase-template complexes. (See, e.g., Korlach, J., et al. (2008) Nucleosides, Nucleotides and Nucleic Acids, 27:1072-1083; and Eid, J. (2009) Science 323:133-138.) The complexes were immobilized in zero-mode waveguides in a reaction mixture containing all necessary buffer and nucleotide analog components for carrying out sequencing-by-synthesis reactions with the exception of a cognate starting base and a metal dication. A Smith-Waterman algorithm was used to perform the alignment of the known sequence of the template with the sequence reads generated in the reaction, and the positions of the sequence reads is graphically illustrated in FIG. 8.

Figure 8:
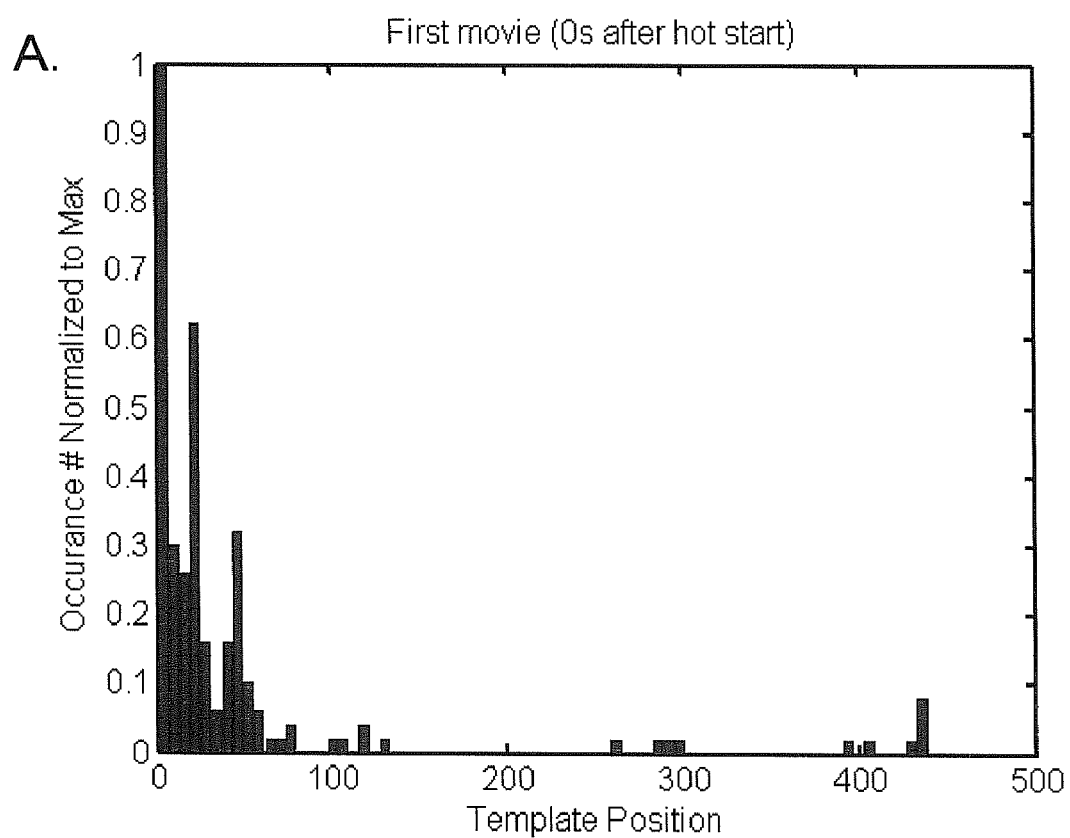
FIG. 8 provides data from single-molecule sequencing-by-synthesis reactions.

Acquisition of the data shown in FIG. 8 was collected as follows. Illumination of the array of zero-mode waveguides was initiated with laser excitation (532 nm and 641 nm laser lines) at t=−5 seconds, and the missing cognate starting base and metal dication (manganese metal) were added at t=0 seconds to simultaneously initiate the sequencing-by-synthesis reactions in all zero-mode waveguides. The reactions were monitored under illumination for 120 seconds at which time the illumination was removed; the sequencing reads generated during that stage of the reaction are shown in FIG. 8A as a function of the template position to which each read maps. At 295 seconds illumination was resumed and data acquisition was reinitiated at 300 seconds and maintained for another 120 second interval; the sequencing reads during this second illuminated period are shown in FIG. 8B. At 595 seconds illumination was resumed and data acquisition was reinitiated at 600 seconds and maintained for another 120 second interval; the sequencing reads during this third illuminated period are shown in FIG. 8C.

As expected, the longer the amount of time before the sequence data is collected (that is, the later the illuminated period), the further into the template the alignments shift, and this shift is a rough function of time since initiation of the reaction. Further, the distribution of sequence reads generated during each subsequent illuminated period becomes more dispersed than the previous illuminated period(s). Further, due to the circular nature of the template, FIG. 8C clearly shows that some polymerases have passed completely around the substrate and are beginning to generate sequence reads from a second pass around the template, thereby generating redundant sequence information for a single template nucleic acid.

What is claimed is:

1. A method of performing an analytical reaction, comprising:
   a) preparing a reaction mixture containing components of the analytical reaction, wherein at least one of the components is a detectable component;
   b) initiating the analytical reaction in the reaction mixture to begin progression of the analytical reaction, wherein the analytical reaction comprises an enzyme selected from the group consisting of a polymerase, a ligase, a ribosome, a nuclease, and a kinase; and
   c) maintaining conditions that allow the analytical reaction to proceed while subjecting the reaction mixture to at least one detection period and at least one non-detection period during the progression of the analytical reaction, wherein the detection period is an illuminated period and the non-detection period is a non-illuminated period, and further wherein the detectable component is present during both said detection period and said non-detection period, thereby performing the analytical reaction.

2. The method of claim 1, further comprising collecting illumination data during the illuminated period, collecting non-illumination data during the non-illuminated period, and further wherein an optical system is used in collecting the illumination data but is not used in collecting the non-illumination data.

3. The method of claim 1, wherein the enzyme is a polymerase and the method further comprises pause or stop points to control the activity of the polymerase during the analytical reaction.

4. The method of claim 1, wherein said subjecting the reaction mixture to at least one detection period and at least one non-detection period during the progression of the analytical reaction results in a change in one or more aspects of the analytical reaction, said aspects selected from the group consisting of processivity, fidelity, rate, and duration.

5. The method of claim 1, wherein the analytical reaction is a sequencing reaction comprising a single nucleic acid template, wherein the sequencing reaction generates sequence reads during the detection period by detecting the detectable component, and does not generate sequence reads during the non-detection period by suspending detection of the detectable component.

6. The method of claim 5, wherein the sequencing reaction comprises at least two detection periods and generates a plurality of noncontiguous sequence reads from the single nucleic acid template.

7. The method of claim 6, wherein the plurality comprises at least three noncontiguous sequence reads.

8. The method of claim 5, wherein the single nucleic acid template comprises multiple repeat sequences.

9. The method of claim 5, wherein the sequencing reaction comprises passage of the single nucleic acid template through a nanopore.

10. The method of claim 5, wherein the sequencing reaction comprises primer extension by a polymerase enzyme and the detectable component is a nucleotide or nucleotide analog.

11. The method of claim 1, wherein the analytical reaction is a processive reaction.

12. The method of claim 11, further comprising collecting detection data in real time during the detection period, collecting non-detection data in real time during the non-detection period, and combining the detection data and the non-detection data to characterize the analytical reaction.

13. The method of claim 1, wherein the detectable component has a detectable label.

14. The method of claim 13, wherein the detectable label is a luminescent, fluorescent, or fluorogenic label.

15. The method of claim 1, wherein the detectable component is a labeled nucleotide or nucleotide analog, and further wherein a concentration of the labeled nucleotide or nucleotide analog in the reaction mixture is greater than a concentration of any unlabeled nucleotide or nucleotide analog present in the reaction mixture throughout the progression of the analytical reaction.

16. The method of claim 1, wherein the detection period and the non-detection period are created without any substitution of components in the analytical reaction during progression of the analytical reaction.

17. The method of claim 1, wherein a plurality of analytical reactions are characterized, and further wherein the plurality of analytical reactions are disposed on a solid support.

18. A method of generating a plurality of noncontiguous sequence reads from a single nucleic acid template molecule, comprising:
  a) preparing a reaction mixture comprising the single template nucleic acid molecule, a polymerase enzyme, and a set of labeled nucleotides or nucleotide analogs, wherein the set comprises at least one type of labeled nucleotide or nucleotide analog for each of the natural nucleobases (A, G, T, and C), and further wherein each type of labeled nucleotide or nucleotide analog in the set comprises a detectable label that distinguishes it from every other type in the set;
  b) initiating the polymerization reaction to begin a first processive incorporation of a plurality of the labeled nucleotides or nucleotide analogs into a nascent nucleic acid strand complementary to the single template nucleic acid molecule;
  c) detecting the first processive incorporation by optical means, thereby generating one of the plurality of noncontiguous sequence reads from the single template nucleic acid template molecule;
  d) performing a buffer exchange to substitute the labeled nucleotides or nucleotide analogs with unlabeled nucleotides or nucleotide analogs;
  e) allowing the polymerization reaction to begin a second processive incorporation of the unlabeled nucleotides or nucleotide analogs without detecting the second processive incorporation of the unlabeled nucleotides or nucleotide analogs;
  f) performing a buffer exchange to substitute the unlabeled nucleotides or nucleotide analogs with the labeled nucleotides or nucleotide analogs;
  g) allowing the polymerization reaction to initiate a third processive incorporation of a plurality of the labeled nucleotides or nucleotide analogs; and
  h) detecting the third processive incorporation by optical means, thereby generating a second of the plurality of noncontiguous sequence reads from the single template nucleic acid molecule.

19. The method of claim 18 further comprising repeating steps d-g, wherein steps d-g are repeated n times to generate (n+2) noncontiguous sequence reads.

* * * * *